United States Patent
Sakamoto et al.

(10) Patent No.: US 9,517,289 B2
(45) Date of Patent: Dec. 13, 2016

(54) WATER-ABSORBING AGENT AND METHOD FOR PRODUCING THE SAME

(75) Inventors: Shigeru Sakamoto, Hyogo (JP); Hiroyuki Ikeuchi, Hyogo (JP); Sayaka Machida, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 894 days.

(21) Appl. No.: 12/680,740

(22) PCT Filed: Nov. 26, 2008

(86) PCT No.: PCT/JP2008/071919
§ 371 (c)(1),
(2), (4) Date: Mar. 29, 2010

(87) PCT Pub. No.: WO2009/075204
PCT Pub. Date: Jun. 18, 2009

(65) Prior Publication Data
US 2010/0240823 A1    Sep. 23, 2010

(30) Foreign Application Priority Data

Dec. 12, 2007 (JP) ................................ 2007-321227

(51) Int. Cl.
| | | |
|---|---|---|
| C08L 57/10 | (2006.01) |
| A61L 15/60 | (2006.01) |
| C08G 65/332 | (2006.01) |
| C08J 3/12 | (2006.01) |
| C08L 71/02 | (2006.01) |
| C08L 101/14 | (2006.01) |
| C08L 33/02 | (2006.01) |

(52) U.S. Cl.
CPC ............ *A61L 15/60* (2013.01); *C08G 65/3322* (2013.01); *C08J 3/12* (2013.01); *C08L 71/02* (2013.01); *C08L 101/14* (2013.01); *C08J 2300/14* (2013.01); *C08L 33/02* (2013.01); *C08L 2205/05* (2013.01)

(58) Field of Classification Search
CPC ................................ C08F 210/16; C08K 5/06
USPC ................................................. 524/543, 376
See application file for complete search history.

(56) References Cited

U.S. PATENT DOCUMENTS

| | | | |
|---|---|---|---|
| 4,076,663 A * | 2/1978 | Masuda et al. ............ 525/54.31 |
| 4,389,513 A * | 6/1983 | Miyazaki ...................... 525/186 |
| 4,625,001 A * | 11/1986 | Tsubakimoto et al. ......... 526/88 |
| 4,654,039 A * | 3/1987 | Brandt et al. ................. 604/368 |
| 5,250,640 A * | 10/1993 | Irie et al. ......................... 526/88 |
| 5,489,647 A | 2/1996 | Kussmaul et al. |
| 6,559,239 B1 * | 5/2003 | Riegel et al. ............... 525/329.7 |
| 7,312,278 B2 * | 12/2007 | Nakashima et al. .......... 525/119 |
| 7,816,301 B2 * | 10/2010 | Ikeuchi et al. ................ 502/402 |
| 7,872,076 B2 * | 1/2011 | Ikeuchi et al. ............. 525/329.7 |
| 2002/0120241 A1 * | 8/2002 | Tyrrell et al. ................. 604/364 |
| 2007/0203280 A1 * | 8/2007 | Okochi ......................... 524/430 |
| 2008/0139693 A1 * | 6/2008 | Ikeuchi et al. ................ 523/111 |
| 2008/0247987 A1 * | 10/2008 | Liggins et al. ............. 424/78.17 |
| 2009/0012488 A1 * | 1/2009 | Braig et al. ................... 604/359 |
| 2009/0131255 A1 * | 5/2009 | Ikeuchi et al. ................ 502/402 |
| 2010/0004418 A1 * | 1/2010 | Braig et al. ................... 526/333 |

FOREIGN PATENT DOCUMENTS

| | | |
|---|---|---|
| JP | 55-084304 | 6/1980 |
| JP | 2002-265511 | 9/2002 |
| WO | 2005/097313 | 10/2005 |
| WO | 2007/037453 | 4/2007 |
| WO | 2007/037454 | 4/2007 |
| WO | 2007/041075 | 4/2007 |
| WO | WO 2007/037453 A1 * | 4/2007 |
| WO | WO 2007 037453 A1 * | 4/2007 |

* cited by examiner

*Primary Examiner* — Mark Eashoo
*Assistant Examiner* — M. Reza Asdjodi
(74) *Attorney, Agent, or Firm* — Dickinson Wright PLLC

(57) ABSTRACT

The present invention provides a water-absorbing agent that includes water-absorbent resin particles as essential components and is suitable for a sanitary material. A water-absorbing agent of the present invention includes water-absorbent resin particles obtained by polymerizing an unsaturated monomer having an acid group. The water-absorbing agent has centrifuge retention capacity (CRC) of 5 to 20 g/g and includes: a compound with a structure unit derived from polyalkyleneglycol other than the unsaturated monomer; and a multivalent metal salt, and accordingly the water-absorbing agent has high saline flow conductivity (SFC) in a range of the above centrifuge retention capacity (CRC).

5 Claims, 3 Drawing Sheets

WATER-ABSORBING AGENT AND METHOD FOR PRODUCING THE SAME

TECHNICAL FIELD

The present invention relates to a water-absorbing agent and a method for producing the same. In particular, the present invention relates to a water-absorbing agent suitable for sanitary materials such as diapers and to a method for producing the same.

BACKGROUND ART

Water-absorbent resin exhibits high absorption rate, a large absorption amount, and a high retaining property with respect to an aqueous solution. Accordingly, for the purpose of absorbing body fluids, the water-absorbent resin has been conventionally used for absorbent cores of sanitary materials such as diapers, if necessary in combination with a fiber material made of cellulose fibers, polyester fibers, polyethylene fibers, or polypropylene fibers etc.

Recently, in response to increasing needs for thinner sanitary materials such as diapers, absorbent cores tend to include more amount of water-absorbent resin. In order to make the sanitary materials further thinner, it is required to replace the fiber materials with water-absorbent resin so as to further increase the amount of the water-absorbent resin in the absorbent cores.

The water-absorbent resin is excellent by nature in absorption and retention of an aqueous solution. However, the fiber material is not excellent in such absorption and retention, in particular not excellent in retention of an aqueous solution, and has abilities different from those of conventional water-absorbent resin. Therefore, in order to provide water-absorbent resin that meets the above requirement, it is necessary to develop water-absorbent resin with abilities of the fiber material included in a conventional absorbent core. Examples of abilities necessary for such water-absorbent resin include: an ability of diffusing an aqueous solution after absorbing the aqueous solution; and an ability of temporarily retaining an aqueous solution after absorbing the aqueous solution. That is, in a case where Centrifuge Retention Capacity (CRC; may be hereinafter abbreviated as "CRC") that is an index for an ability of absorbing and retaining an aqueous solution is in a predetermined range lower than Centrifuge Retention Capacity (CRC) desired for conventional water-absorbent resin, in order that the water-absorbing agent absorbs an aqueous solution and then swiftly diffuses the aqueous solution in a perpendicular direction or a lateral direction, it is required to develop water-absorbent resin with high Saline Flow Conductivity (SFC; may be hereinafter abbreviated as "SFC") that is an index for an ability of causing the aqueous solution to permeate in swollen gels under pressure.

An example of such water-absorbent resin is an aqueous solution-absorbing agent with CRC ranging from 5 to 25 g/g and SFC being 1216 $cm^3 \cdot s \cdot 10^{-7}/g$ or more (see Patent Document 1 etc. for example). It is disclosed that such aqueous solution-absorbing agent can be obtained by polymerizing water-soluble ethylenically unsaturated monomer including a carboxyl group in the presence of an internal crosslinking agent including at least four functional groups each capable of forming a covalent bond with a carboxyl group.

Further, in order to provide a water-absorbing agent with increased liquid-permeability without dropping absorption capacity in a range of higher CRC, there is disclosed a water-absorbing agent that includes as a main component water-absorbent resin with a crosslinked structure obtained by polymerizing a carboxyl group-containing unsaturated monomer. The water-absorbing agent is internal crosslinked with non-polymeric compounds with at least four functional groups each capable of forming a covalent bond with a carboxyl group (see Patent Document 2 for example).

Although not regarding the water-absorbent resin with the abilities of a fiber material of an absorbent core, some documents report partially neutralized poly(acrylic acid) including polyethylene glycol. For example, regarding a uncrosslinked partially neutralized poly(acrylic acid) used in a sticking agent, it is reported that adding polyethylene glycol to a monomer aqueous solution containing partially neutralized acrylic acid and polymerizing the resultant results in uncrosslinked partially neutralized poly(acrylic acid) hydrogel that has excellent mold-releasability from a manufacture device such as a receptacle (see Patent Document 3 for example). Further, there is disclosed a method for performing aqueous solution polymerization on partially neutralized acrylic acid in the presence of polyethylene glycol with 400 molecular weight, in order to provide alkaline metal salts of crosslinked poly(acrylic acid) that are excellent in absorbency and viscosity-increasing property, that does not exhibit surface tackiness at a time of touching a liquid to be absorbed, that is adjusted to be in a safe range for human skin, and that is suitable for water-absorbent resin (see Patent Document 4 for example). Patent Document 4 describes that when water-soluble polyhydric alcohol such as polyethylene glycol is used as a crosslinking agent instead of a water-soluble polyfunctional vinyl monomer, a crosslinked structure can be formed by an esterification reaction between a hydroxyl group of the water-soluble polyhydric alcohol and carboxyl group. Furthermore, Patent Document 5 discloses a hydrophilic graft polymer capable of swelling and describes a graft polymerization between an acrylic acid and a polyalkylene oxide compound.

[Patent Document 1] International Publication No. 2007/037453, pamphlet
[Patent Document 2] International Publication No. 2007/037454, pamphlet
[Patent Document 3] Japanese Unexamined Patent Publication No. 2002-265511 (Tokukai 2002-265511; published on Sep. 18, 2002)
[Patent Document 4] Japanese Unexamined Patent Publication No. 1980-84304 (Tokukaisho 55-84304; published on Jun. 25, 1980)
[Patent Document 5] Japanese Unexamined Patent Publication No. 1993-239156 (Tokukaihei 5-239156; published on Sep. 17, 1993)

DISCLOSURE OF INVENTION

Problems to be Solved by the Invention

However, there is an antithetic relation between Centrifuge Retention Capacity (CRC) and Saline Flow Conductivity (SFC), resulting in a problem that when Saline Flow Conductivity (SFC) is increased, Centrifuge Retention Capacity (CRC) drops. As for water-absorbent resin with relatively low CRC that can be used in place of a fiber material, the same problem is seen in a range of the CRC.

An object of the present invention is to provide a water-absorbing agent that has an improved relation between Centrifuge Retention Capacity (CRC) and Saline Flow Conductivity (SFC) and that has higher SFC in a range where CRC is 20 g/g or less, which range is suitable for water-absorbent resin having properties of the fiber material.

Means to Solve the Problems

In order to solve the foregoing problem, the water-absorbing agent of the present invention is a water-absorbing agent, including water-absorbent resin particles obtained by polymerizing an acid group-containing unsaturated monomer, the water-absorbing agent having Centrifuge Retention Capacity (CRC) ranging from 5 to 20 g/g, and including (i) a compound that includes a constitutional unit derived from polyalkyleneglycol and that is other than an unsaturated monomer and (ii) polyvalent metal salt.

It is preferable to arrange the water-absorbing agent of the present invention so that the water-absorbent resin particles are surface-crosslinked.

It is preferable to arrange the water-absorbing agent of the present invention so that Saline Flow Conductivity (SFC) is 400 $cm^3 \cdot s \cdot 10^{-7}$/g or more.

It is preferable to arrange the water-absorbing agent of the present invention so that the compound that includes a constitutional unit derived from polyalkyleneglycol and that is other than an unsaturated monomer does not include a radical polymerizable group.

It is preferable to arrange the water-absorbing agent of the present invention so that the water-absorbent resin particles are obtained by polymerization in a presence of an internal crosslinking agent containing an unsaturated monomer including a constitutional unit derived from polyalkyleneglycol.

It is preferable to arrange the water-absorbing agent of the present invention so that weight-average molecular weight of the compound that includes a constitutional unit derived from polyalkyleneglycol and that is other than an unsaturated monomer ranges from 1000 to 50000.

In order to solve the foregoing problem, the method of the present invention for producing a water-absorbing agent is a method for producing a water-absorbing agent with Centrifuge Retention Capacity (CRC) ranging from 5 to 20 g/g, the method including the steps of: (A) producing a crosslinked polymer hydrogel by polymerizing an acid group-containing unsaturated monomer in a presence of an internal crosslinking agent; (B) obtaining water-absorbent resin particles (water-absorbent resin particles not surface-crosslinked) by drying the crosslinked polymer hydrogel obtained in the step (A); and (C) obtaining surface-crosslinked water-absorbent resin particles by surface-crosslinking the water-absorbent resin particles (not surface-crosslinked) obtained in the step (B), the method further including the steps of: adding the compound that includes a constitutional unit derived from polyalkyleneglycol and that is other than an unsaturated monomer; and adding polyvalent metal salt.

It is preferable to arrange the method of the present invention so that the step of adding the compound that includes a constitutional unit derived from polyalkyleneglycol and that is other than an unsaturated monomer is carried out before and/or in the step (A).

It is preferable to arrange the method of the present invention so that the step of adding the compound that includes a constitutional unit derived from polyalkyleneglycol and that is other than an unsaturated monomer is carried out in the step (C).

It is preferable to arrange the method of the present invention so that the step of adding the polyvalent metal salt is carried out in the step (C) or after the step (C).

In order to solve the foregoing problem, the method of the present invention for producing a water-absorbing agent is a method for producing a water-absorbing agent with Centrifuge Retention Capacity (CRC) ranging from 5 to 20 g/g, the method including the step of: adding polyvalent metal salt to water-absorbent resin particles that are obtained by polymerizing an acid group-containing unsaturated monomer and that include a compound that includes a constitutional unit derived from polyalkyleneglycol and that is other than an unsaturated monomer.

It is preferable to arrange the method of the present invention so that the compound that includes a constitutional unit derived from polyalkyleneglycol and that is other than an unsaturated monomer does not include a radical polymerizable group.

It is preferable to arrange the method of the present invention so that weight-average molecular weight of the compound that includes a constitutional unit derived from polyalkyleneglycol and that is other than an unsaturated monomer ranges from 1000 to 50000.

Effect of the Invention

As described above, the water-absorbing agent of the present invention is a water-absorbing agent, including water-absorbent resin particles obtained by polymerizing an acid group-containing unsaturated monomer, the water-absorbing agent having Centrifuge Retention Capacity (CRC) ranging from 5 to 20 g/g, and including (i) a compound that includes a constitutional unit derived from polyalkyleneglycol and that is other than an unsaturated monomer and (ii) polyvalent metal salt. Therefore, when an absorbent core in a sanitary material such as a diaper includes the water-absorbing agent of the present invention, it is possible to realize excellent liquid permeability between swollen gels and to diffuse an aqueous solution in a wider range. This yields notable effects in the purposes of sanitary materials and others, such as replacing a fiber material used in an absorbent core in a sanitary material with the water-absorbing agent of the present invention to make the sanitary material thinner.

REFERENCE NUMERALS

Figure 1:
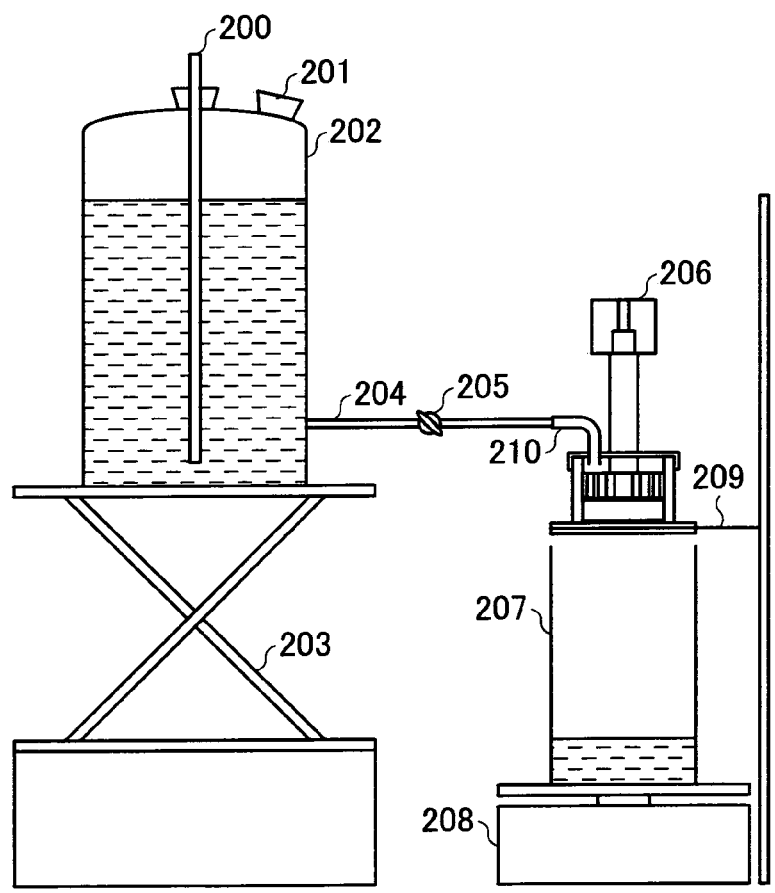
FIG. 1 is a cross sectional view schematically illustrating a measurement device used for measuring SFC.

200: glass tube with open end and rubber plug section
201: rubber plug section
202: storage tank
203: labo jack
204: glass tube with valve
205: valve
206: SFC device
207: collection tank
208: scale
209: supporter
210: flexible tube
211: weight 212: piston
213: cover
214: cylinder
215: piston head
216: wiremesh with 400 meshes
217: aqueous solution absorbent core having been swollen

BEST MODE FOR CARRYING OUT THE INVENTION

The following details the present invention. The scope of the present invention is not restrained by the following explanation and the following examples may be suitably changed within the scope of the present invention.

Furthermore, in the present invention, (a) mass average particle diameter (D50) and logarithmic standard deviation (σξ) of particle diameter distribution, (b) Centrifuge Retention Capacity (CRC), (c) solid content, (d) Saline Flow Conductivity, (e) molecular weight and elution weight of polyethyleneglycol (PEG) having eluted from water-absorbent resin particles and a water-absorbing agent, (f) extractable polymer content, and (g) amount of polyvalent metal salt contained in a water-absorbing agent (on polyvalent metal basis (cation basis)), are values measured through methods descried in the following Examples. Furthermore, in the present invention, weight-average molecular weight is a value measured through a method that is the same as the method, described in the following Examples, for measuring molecular weight of polyethyleneglycol (PEG) having eluted from a water-absorbing agent. In the present invention, "weight" is a synonym for "mass" and "weight %" is a synonym for "mass %".

(1) Water-Absorbing Agent of the Present Invention

The water-absorbing agent of the present invention is a water-absorbing agent containing water-absorbent resin particles obtained by polymerizing an acid group-containing unsaturated monomer. The water-absorbing agent has Centrifuge Retention Capacity (CRC) ranging from 5 to 20 g/g and includes: a compound that has a constitutional unit derived from polyalkyleneglycol and that is other than the unsaturated monomer; and polyvalent metal salt. In the present invention, "including a compound that has a constitutional unit derived from polyalkyleneglycol and that is other than the unsaturated monomer; and polyvalent metal salt" means that a compound that has a constitutional unit derived from polyalkyleneglycol and that is other than the unsaturated monomer and polyvalent metal salt exist on at least one of the inside, the surface, and vicinity of the surface of the water-absorbent resin particles. It is preferable that a compound that has a constitutional unit derived from polyalkyleneglycol and that is other than the unsaturated monomer and polyvalent metal salt exist while attached to the water-absorbent resin particles and it is preferable that the compound and the polyvalent metal salt are free without forming a chemical bond with the water-absorbent resin particles or are separable from the water-absorbent resin particles.

Furthermore, the compound that has a constitutional unit derived from polyalkyleneglycol and that is "other than the unsaturated monomer" is a compound that has a constitutional unit derived from polyalkyleneglycol and that is not an unsaturated monomer. Here, the unsaturated monomer is a monomer with double bonds, whose weight-average molecular weight is less than 1000, more preferably less than 800.

In the present invention, the water-absorbing agent indicates an absorbing and solidifying agent for an aqueous solution, including water-absorbent resin particles as a main component. Here, "including as a main component" indicates that the amount of contained water-absorbent resin particles is 50 weight % or more with respect to the whole amount of the water-absorbing agent. The amount of contained water-absorbent resin particles is preferably 60 to 99.9 weight %, more preferably 70 to 99.9 weight %, further preferably 80 to 99.9 weight %, and further more preferably 90 to 99.9 weight %.

Here, the aqueous solution is not particularly limited as long as it contains water. Examples of the aqueous solution include: water; urine; blood; feces; waste solution; moisture and vapor; ice; mixture of water and organic solvent and/or inorganic solvent; rain water; and ground water. In particular, the water-absorbing agent of the present invention is preferably an absorbing and solidifying agent for urine, particularly human urine.

In the following, explanations of the water-absorbing agent of the present invention will be made as to (1-1) water-absorbent resin particles included in the water-absorbing agent of the present invention, (1-2) a compound that includes a constitutional unit derived from polyalkyleneglycol and that is other than an unsaturated monomer, (1-3) polyvalent metal salt, (1-4) other components, and (1-5) properties of the water-absorbing agent of the present invention.

(1-1) Water-Absorbent Resin Particles Included in the Water-Absorbing Agent of the Present Invention The water-absorbent resin particles included in the water-absorbing agent of the present invention are particles of water-absorbent resin having an internal crosslinked structure obtained by polymerizing an acid group-containing unsaturated monomer.

Here, the water-absorbent resin is a water-swelling and water-insoluble crosslinked polymer, capable of forming a hydrogel. Here, "water-swelling" generally means, for example, a property of absorbing a large amount of water that is preferably 5 times or more, more preferably 10 times or more, still more preferably 20 times or more, and particularly preferably 50 to 1000 times or more with respect to one's own weight in ion-exchanged water. A "water-swelling" crosslinked polymer is a crosslinked polymer whose "Centrifuge Retention Capacity in ion-exchanged water" is 5 or more, more preferably 10 or more, still more preferably 20 or more, and particularly preferably 50 to 1000. "Centrifuge Retention Capacity in ion-exchanged water" is measured through the same method as a later-mentioned method for measuring Centrifuge Retention Capacity (CRC) except that an object to be measured is 0.020 g of water-absorbent resin particles or a water-absorbing agent and measurement is performed in ion-exchanged water.

Furthermore, "water-insoluble" indicates that the amount of uncrosslinked extractable polymer content (water-soluble macromolecule) in the water-absorbent resin is preferably 0 to 50 weight % or less, more preferably 20 weight % or less, still more preferably 10 weight % or less, and particularly preferably 5 weight % or less. A general method for measuring an amount of extractable polymer content will be described in Examples.

Furthermore, it is preferable that 100% of water-absorbent resin particles used in the present invention have a particle shape. Examples of the particle shape include: a sphere shape; agglomeration of spheres; a compressed sphere shape; an irregularly pulverized shape; a shape obtained by granulating the irregularly pulverized shape; and a foamed shape with pores.

<Water-Absorbent Resin Particles Obtained by Polymerizing Acid Group-Containing Unsaturated Monomer>

In the present invention, water-absorbent resin particles are preferably particles of water-absorbent resin having an internal crosslinked structure obtained by polymerizing an acid group-containing unsaturated monomer. The acid group-containing unsaturated monomer is not particularly limited as long as it is a monomer containing an acid group such as a carboxyl group and a sulfo group. In particular, a carboxyl group-containing monomer is preferable in terms of water-absorption properties. Furthermore, in the present invention, a monomer containing a group which becomes a carboxyl group through hydrolysis carried out after polymerization, such as acrylonitrile, is regarded as a carboxyl group-containing monomer. However, it is preferable to use a carboxyl group-containing monomer that contains a carboxyl group at a time of polymerization.

Examples of water-absorbent resin obtained by polymerizing an acid group-containing unsaturated monomer include: a polymer obtained by polymerizing and crosslinking a carboxyl group-containing unsaturated monomer such as (meta)acrylic acid, maleic anhydride, maleic acid, fumaric acid, crotonic acid, itaconic acid, and cinamic acid and/or salt (neutralized product) thereof; hydrolysate of starch-acrylonitrilegraft polymer; starch-acrylic acid graft polymer; saponified vinyl acetate-acrylic acid ester copolymer; hydrolysate of acrylonitrile copolymer or acrylamide copolymer, or crosslinked product thereof; crosslinked denatured polyvinylalcohol containing a carboxyl group; crosslinked isobutylene-maleic anhydride copolymer; and combination of two or more of them.

Preferable examples of the water-absorbent resin include: partially neutralized crosslinked polyacrylic acid polymer disclosed in U.S. Pat. Nos. 4,625,001, 4,654,039, 5,250,640, and 5,275,773 and European Patent No. 456136 etc.; starch-acrylic acid graft polymer that is crosslinked and partially neutralized, disclosed in U.S. Pat. No. 4,076,663; isobutylene-maleic acid copolymer disclosed in U.S. Pat. No. 4,389,513; saponified vinyl acetate-acrylic acid copolymer disclosed in U.S. Pat. No. 4,124,748; hydrolysate of acrylamide (co)polymer disclosed in U.S. Pat. No. 3,959,569; and hydrolysate of acrylonitrile polymer disclosed in U.S. Pat. No. 3,935,099.

Among them, the water-absorbent resin is more preferably a crosslinked polyacrylic acid (salt) polymer or a similar polymer obtained by polymerizing a monomer including acrylic acid and/or salt (neutralized product) thereof as a main component.

In the present invention, the crosslinked polyacrylic acid (salt) polymer or a similar polymer is a polymer with an internal crosslinked structure that is obtained by polymerizing a monomer (except for a crosslinking agent) containing preferably 50 to 100 mol %, more preferably 70 to 100 mol %, and still more preferably 90 to 100 mol % of acrylic acid and/or salt thereof.

Furthermore, it is preferable that 45 to 85 mol % of a carboxyl group included in the crosslinked polyacrylic acid (salt) polymer or a similar polymer is neutralized to form salt. In other words, a rate of neutralization of an acid group included in particles of the water-absorbent resin ranges preferably from 45 to 85 mol %, more preferably from 50 to 85 mol %, still more preferably from 55 to 80 mol %, and particularly preferably from 60 to 75 mol %. The salt is one or more of: alkali metal salt such as sodium salt, potassium salt, and lithium salt; ammonium salt; and amine salt. Neutralization of an acid group for forming salt may be performed in a state of a monomer before polymerization, or in a state of a polymer during polymerization or after polymerization, or both in the two states.

The rate of neutralization of an acid group in the water-absorbent resin particles can be calculated based on (i) an amount of an acid group-containing unsaturated monomer that has not been neutralized and (ii) an amount of all bases used in neutralization before polymerization, during polymerization, and/or after polymerization. Furthermore, the rate of neutralization may be obtained by extracting extractable polymer content from the water-absorbent resin particles and titrating the extractable polymer content.

The water absorbent resin particles preferably used in the present invention may be obtained by copolymerizing (i) an acid group-containing unsaturated monomer (acrylic acid and/or salt thereof in a case of crosslinked polyacrylic acid (salt) polymer or similar polymer) as a main component and (ii) other monomer if necessary.

Specific examples of other monomer include: anionic unsaturated monomer such as methacrylic acid, maleic acid (maleic anhydride), fumaric acid, crotonic acid, itaconic acid, vinyl sulfonic acid, styrene sulfonic acid, 2-(meta)acrylamide-2-methylpropanesulfonic acid, (meta)acryloxyalkanesulfonic acid, 2-(meta)acryloyl ethane sulfonic acid, and 2-(meta)acryloyl propanesulfonic acid, and its alkaline metal salt or its ammonium salt; nonionic hydrophilic group-containing unsaturated monomer such as (meth)acrylamide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl(meth)acrylate, methoxypolyethylene glycol (meth)acrylate, polyethylene glycol (meth)acrylate, vinyl pyridine, N-vinyl pyrrolidone, N-acryloyl piperidine, N-acryloyl pyrrolidine, and N-vinylacetamide; cationic unsaturated monomer such as N,N-dimethylaminoethyl(meth)acrylate, N, N-diethylaminoethyl(meth)acrylate, N, N-dimethylaminopropyl(meth)acrylate, N, N-dimethylaminopropyl(meth)acrylamide, and quaternary salt thereof; isobutylene; and lauryl(meth)acrylate. Amount of a polymer other than these acrylic acid and/or salt thereof ranges preferably from 0 to 30 mol %, more preferably from 0 to 10 mol % with respect to all monomers.

<Crosslinked Structure>

The water-absorbent resin particles included in the water-absorbing agent of the present invention have a crosslinked structure at least inside the water-absorbent resin, preferably inside and at a surface of the water-absorbent resin. This is preferable since it allows gel strength after polymerization to be higher, increasing handleability of the water-absorbent resin hydrogel.

The internal crosslinked structure may be a self-crosslinked structure without a crosslinking agent or may be a structure that is obtained by copolymerizing or reacting an internal crosslinking agent that includes two or more polymerizable ethylenic double bonds or two or more functional groups in one molecule. The functional group as used herein means a reactive group in a molecule and includes a covalent-bondable functional group and an ionic-bondable functional group. The functional group is not particularly limited as long as it can bind to an acid group of the water-absorbent resin. Examples of the functional group include a hydroxyl group, an amino group, an epoxy group, an oxetane group, an ethyleneimine group (aziridine group), an isocyanate group, oxazoline, cyclocarbonate, oxazolidinone, cyclic urea, azetidinium base, and chlorohydrin.

Specific examples of the internal crosslinking agent with two or more polymerizable ethylenic double bonds include N,N'-methylenebis(meth)acrylamide, (poly)ethylene glycol di(meth)acrylate, (poly)propylene glycol di(meth)acrylate, trimethylolpropane tri(meth)acrylate, glycerine tri(meth)acrylate, glycerine acrylate methacrylate, ethylene oxide denatured trimethylolpropane tri(meth)acrylate, pentaerythritol hexa(meth)acrylate, triallyl cyanurate, triallyl isocyanurate, triallyl phosphate, triallyl amine, and poly (meth) allyloxy alkane.

Examples of the internal crosslinking agent with two or more functional groups, i.e., the internal crosslinking agent with two or more covalent-bondable functional groups or ionic-bondable functional groups, include: a polyhydric alcohol compound, such as ethylene glycol, diethylene glycol, propylene glycol, triethylene glycol, tetraethylene glycol, 1,3-propanediol, dipropylene glycol, 2,2,4-trimethyl-1,3-pentanediol, glycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylol propane, diethanolamine, triethanolamine, polyoxypropylene, and oxyetylene-oxypropylene block copolymer; polyhydric alcohol such as polyglycerin and pentaerythritol; sugar alcohol such as erythritol, xylitol, sorbitol, mannitol, maltitol, lactitol, and oligosaccharide alcohol; aldose such as xylose, glucose, gulose, mannose, and idose; ketose such as fructose and sorbose; triethylenetetramine, tetraethylenepentamine, pentaethylenehexamine, 2-amino-2 hydroxymethyl-1,3-propanediol, and N,N-bis (2-hydroxyethyl)ethylenediamine; polyvalent metal compound such as hydroxide and chloride of zinc, calcium, magnesium, aluminum, iron, or zirconium; polyglycidyl ether such as (poly)ethleneglycol diglycidyl ether and glycerol diglycidyl ether; ethylenediamine; alkylenecarbonate such as etylenecarbonate and propylene carbonate; and gycidyl(meth)acrylate.

These internal crosslinking agents may be used in the singular or in combinations with each other. Among them, it is preferable that the water-absorbent resin used in the present invention is crosslinked by an internal crosslinking agent with two or more polymerizable ethylenic double bonds in terms of water-absorbent property of the water-absorbent resin or the water-absorbing agent.

It is more preferable that the water-absorbent resin used in the present invention is crosslinked by both an internal crosslinking agent with four or more functional groups capable of forming a covalent bond with an acid group and an internal crosslinking agent with two or more polymerizable ethylenic double bonds. This allows further increasing liquid-permeability of the obtained water-absorbent resin and water-absorbing agent. Here, the internal crosslinking agent with four or more functional groups capable of forming a covalent bond with an acid group is preferably one of the internal crosslinking agents as described above. Among them, it is more preferable that the internal crosslinking agent is one of sugar alcohol. It is still more preferable that the internal crosslinking agent is one of erythritol, xylitol, and sorbitol. They are preferable in terms of very high safety, too.

The water-absorbent resin used in the present invention is at least required to be internally crosslinked. It is more preferable that the water-absorbent resin is surface crosslinked as well as internally crosslinked.

Here, surface crosslinking of the water-absorbent resin means providing, on a surface layer (vicinity of surface: vicinity that is several 10 μm or less away from the surface in general) of the water-absorbent resin, an area where crosslinking density is higher than other areas. A high crosslinking layer may be formed through radical crosslinking on the surface or surface polymerization, or surface crosslinking may be performed through crosslinking reaction with the surface crosslinking agent.

Examples of the surface crosslinking agent for the surface crosslinking include various organic crosslinking agents and inorganic crosslinking agents. In terms of physical properties, it is preferable to use a crosslinking agent capable of reacting with an acid group included in the water-absorbent resin, particularly an organic surface crosslinking agent, in general, a polyhydric alcohol compound, an epoxy compound, a polyamine compound, a condensate of a polyamine compound with a haloepoxy compound, an oxazoline compound, a monooxazolidinone compound, a dioxazolidinone compound, a polyoxazolidinone compound, an alkylenecarbonate compound etc. Specifically, surface crosslinking agents disclosed in U.S. Pat. No. 6,228,930 specification, U.S. Pat. No. 6,071,976 specification, U.S. Pat. No. 6,254,990 specification etc. may be used. More specifically, examples of the surface crosslinking agents include: polyhydric alcohol compounds, such as ethylene glycol, diethylene glycol, triethylene glycol, tetraethylene glycol, monopropylene glycol, 1,3-propanediol, dipropylene glycol, 2,3,4-trimethyl-1,3-pentanediol, glycerin, polyglycerin, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyamine compounds such as ethylenediamine, diethylenetriamine, triethylenetetramine, tetraethylenepentamine, pentaethylenehexamine, polyethylenimine, and polyamidopolyamine; haloepoxy compounds such as epichlorohydrin, epibromohydrin and α-methylepichlorohydrin; condensates between the above polyamine compounds and the above haloepoxy compounds; oxazolidinone compounds such as 2-oxazolidinone (U.S. Pat. No. 6,559,239); oxetane compounds; cyclic urea compounds; and alkylene carbonate compounds such as ethylene carbonate (U.S. Pat. No. 5,409,771). However, there is no particular limitation. In order to maximize the effect of the present invention, of these crosslinking agents, it is preferable to use at least one selected from the oxetane compounds (US 2002/72471), the cyclic urea compounds, and the polyhydric alcohols, it is more preferable to use at least one selected from an oxetane compound having 2 to 10 carbon atoms and polyhydric alcohol having 2 to 10 carbon atoms, and it is still more preferable to use polyhydric alcohol having 3 to 8 carbon atoms. Further, it is preferable to use a method for surface crosslinking with a monomer including a crosslinking agent (Japanese Patent No. 2530668), a method for surface crosslinking with a radical initiator (Japanese Unexamined Patent Publication No. 1988-99211 (Tokukaisho 63-99211)), a method for surface crosslinking with a radical initiator and a monomer (US 2005-0048221) etc.

(1-2) A Compound that Includes a Constitutional Unit Derived From Polyalkyleneglycol and that is Other than an Unsaturated Monomer The water-absorbing agent according to the present invention includes as an essential component a compound that includes a constitutional unit derived from polyalkyleneglycol and that is other than an unsaturated monomer. It is preferable that the compound exists while being attached to the water-absorbent resin particles and it is preferable that the compound is free without forming a chemical bond with the water-absorbent resin particles or is separable from the water-absorbent resin particles. Further, the compound is required to exist on at least one of the inside, the surface, and vicinity of the surface of the water-absorbent resin particles. It is particularly preferable that the compound is included in the surface. Whether the compound that includes a constitutional unit derived from polyalkyleneglycol and that is other than an unsaturated monomer is included in the surface or not can be easily determined by performing surface cleaning or polishing of the water-absorbing agent.

When the compound is included as an essential component, it is possible to obtain a water-absorbing agent that has an improved relation between Centrifuge Retention Capacity (CRC) and Saline Flow Conductivity (SFC) and high SFC in a range where CRC is 20 g/g or less.

The compound that includes a constitutional unit derived from polyalkyleneglycol and that is other than an unsaturated monomer is not particularly limited as long as it includes preferably 50 to 100 mass %, more preferably 60 to 100 mass %, and still more preferably 80 to 100 mass % of a constitutional unit derived from polyalkyleneglycol, with respect to the whole molecules of the compound. Examples of the compound include polyalkyleneglycol, an ester compound of polyalkyleneglycol, and an ether compound of polyalkyleneglycol.

As for an alkylene unit of polyalkyleneglycol (HO—$((CH_2)_n$—$O)_m$—H) from which the compound derives, the number of carbon atoms, i.e. n in the above general formula, preferably ranges from 1 to 10, more preferably ranges from 2 to 6, still more preferably ranges from 2 to 3, and particularly preferably 2. The compound may be a homopolymer, a block polymer, or a random copolymer. Furthermore, the number of repetition of oxyalkylene unit, i.e. m in the above general formula is 2 or more, more preferably 5 or more, and still more preferably 10 or more. An end of the compound may be OH or may be modified.

In particular, the compound that includes a constitutional unit derived from polyalkyleneglycol and that is other than an unsaturated monomer, used in the water-absorbing agent of the present invention, is more preferably a compound having one or more hydroxyl groups derived from polyalkyleneglycol in its molecular chains. Examples of the compound include: polyalkyleneglycol such as polyethyleneglycol, polypropyleneglycol, polyethyleneglycol-polypropyleneglycol copolymer; polyalkyleneglycolmonoalkylether such as polyethyleneglycolmonoalkylether and polypropyleneglycolmonoalkylether; and polyalkyleneglycol mono fatty acid ester such as polyethyleneglycol mono fatty acid ester and polypropyleneglycol mono fatty acid ester. It is preferable to use the compound having one or more hydroxyl groups derived from polyalkyleneglycol in its molecular chains since it results in a water-absorbing agent with higher Saline Flow Conductivity (SFC).

Patent Document 5 describes graft polymerization of acrylic acid and a polyalkyleneoxide compound, and describes, as an example of the polyalkyleneoxide compound, a compound obtained by reacting polyethyleneglycol with monochloroacetic acid etc. Such a compound is likely to be graft-polymerized and accordingly less likely to elute. In contrast, in the present invention, the compound that includes a constitutional unit derived from polyalkyleneglycol and that is other than an unsaturated monomer is likely to elute. Furthermore, the water-absorbing agent of the present application includes the compound that includes a constitutional unit derived from polyalkyleneglycol and that is other than an unsaturated monomer and polyvalent metal salt and accordingly yields the effect of the present invention. In this point, the water-absorbing agent of the present invention is entirely different from the graft polymer described in Patent Document 5.

It is preferable that the compound that includes a constitutional unit derived from polyalkyleneglycol and that is other than an unsaturated monomer, used in the water-absorbing agent of the present invention, does not include a radical polymerizable group. Here, the radical polymerizable group is not particularly limited. An example of the radical polymerizable group is a polymerizable unsaturated ethylenic double-bond group such as a vinyl group and an allyl group. Consequently, the compound exists while being attached to the water-absorbent resin particles and the compound is free without forming a chemical bond with the water-absorbent resin particles or is separable from the water-absorbent resin particles without forming an internal crosslinked structure in the water-absorbent resin particles. This yields the effect of the present invention.

Furthermore, in a case where the compound includes two or more radical polymerizable groups in its molecular chains, there is a possibility that polymerization of an acid group-containing unsaturated monomer mainly used in the present invention cannot be controlled depending on what compound that includes a constitutional unit derived from polyalkyleneglycol and that is other than an unsaturated monomer is used. This is not preferable since a resulting water-absorbing agent does not have a desired water absorption property. That is, since an internal crosslinking agent is used in producing water-absorbent resin particles used in the water-absorbing agent of the present invention, when the compound having two or more radical polymerizable groups is used in a polymerization process, the compound serves as an additional internal crosslinking agent, resulting in prevention of the effect of the present invention, uncontrollability of polymerization due to too much internal crosslinking agent, and great reduction in absorption capacity.

The alkyl group in the polyalkyleneglycolmonoalkylether may be linear, branched, or cyclic alkyl group. Among them, the linear alkyl group is preferable. The number of carbon atoms of the alkyl group is not particularly limited, but preferably ranges from 2 to 3000, and more preferably ranges from 2 to 1000.

Further, a fatty acid in the polyalkyleneglycol mono fatty acid ester is not particularly limited, but is preferably a saturated fatty acid for the above reason. Further, the number of carbon atoms of the fatty acid is not particularly limited, but preferably ranges from 2 to 3000 and more preferably ranges from 2 to 1000. A hydrocarbon portion of the fatty acid may be linear or branched. More specifically, examples of the fatty acid include ethanoic acid (acetic acid), propanoic acid (propionic acid), butanoic acid (butyric acid), 2-methylpropionic acid (isobutyric acid), pentanoic acid (valeric acid), 3-methylbutanoic acid (isovaleric acid), 2,2-dimethylpropionic acid (pivalic acid), hexanoic acid (caproic acid), heptanoic acid (enanthic acid), octanoic acid (caprylic acid), nonaoic acid (pelargonic acid), decanoic acid (capric acid), dodecanoic acid (lauric acid), hexadecanoic acid (palmitic acid), heptadecanoic acid (margaric acid), octadecanoic acid (stearic acid), nonadecanoic acid (tuberculostearic acid), icosanoic acid (arachidic acid), docosanoic acid (behenic acid), tetradocosanoic acid (lignoceric acid), hexadocosanoic acid (cerotic acid), and octadocosanoic acid (montanic acid, melissic acid).

These compounds including a constitutional unit derived from polyalkyleneglycol other than an unsaturated monomer may be used in the singular or two or more of them may be used in combination.

Furthermore, weight-average molecular weight of the compound that includes a constitutional unit derived from polyalkyleneglycol and that is other than an unsaturated monomer, used in the present invention, ranges preferably from 500 to 50000, more preferably from 1000 to 50000, still more preferably from 1000 to 20000, and particularly preferably from 1000 to 6000. The weight-average molecular weight of the compound being 500 or more is preferable and being 1000 or more is more preferable since it results in a water-absorbing agent with high Saline Flow Conductivity (SFC). Furthermore, the weight-average molecular weight of the compound being 6000 or less is preferable since it ensures excellent handleability and is advantageous in costs. The compound that includes a constitutional unit derived from polyalkyleneglycol and that is other than an unsaturated monomer, included in the water-absorbing agent, ranges preferably from 0.05 to 5 mass %, more preferably from 0.1 to 4 mass %, with respect to the water-absorbing agent.

The compound that includes a constitutional unit derived from polyalkyleneglycol and that is other than an unsaturated monomer, included in the water-absorbing agent, ranges preferably from 0.05 to 5 mass % since this range results in a water-absorbing agent that has an improved relation between Centrifuge Retention Capacity (CRC) and Saline Flow Conductivity (SFC) and high SFC in a range of CRC being 20 g/g or less. Further, when the compound is more than 5 mass %, the relation between CRC and SFC becomes bad and results in high costs, which is not preferable.

It is deemed that most (at least 50%, preferably 70% or more) of the compound that includes a constitutional unit derived from polyalkyleneglycol and that is other than an unsaturated monomer exist without forming a covalent bond with water-absorbent resin particles in the water-absorbing agent of the present invention.

The quantity of the compound without binding with the water-absorbent resin can be determined by extracting an extractable polymer content from the water-absorbing agent and analyzing the extracted content through gel permeation chromatography (GPC) etc. The method for the extraction is not particularly limited and may be suitably selected from conventional known methods. An example of the method is such that a water-absorbing agent is stirred in pure water for 16 hours or more, the aqueous solution is filtered to obtain an extract solution as a filtrate, and the extract solution is analyzed through gel permeation chromatography etc.

(1-3) Polyvalent Metal Salt

The water-absorbing agent of the present invention includes polyvalent metal salt as an essential component. This results in a water-absorbing agent that has an improved relation between Centrifuge Retention Capacity (CRC) and Saline Flow Conductivity (SFC) and high SFC in a range of CRC being 20 g/g or less. When the water-absorbing agent includes only the polyvalent metal salt, SFC of the water-absorbing agent increases. However, when the water-absorbing agent includes both the compound that includes a constitutional unit derived from polyalkyleneglycol and that is other than an unsaturated monomer and the polyvalent metal salt, the SFC of the water-absorbing agent greatly increases, which is a remarkable effect.

Preferable examples of the polyvalent metal salt used in the present invention include aluminum chloride, polyaluminum chloride, aluminum sulfate, aluminum nitrate, potassium aluminum bisulfate, sodium aluminum bisulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, zirconium nitrate, zirconium ammonium carbonate, zirconium potassium carbonate, and zirconium sodium carbonate. Among them, the polyvalent metal salt used in the present invention is more preferably an aluminum compound. More preferable examples of the polyvalent metal salt include aluminum chloride, polyaluminum chloride, aluminum sulfate, aluminum nitrate, potassium aluminum bisulfate, sodium aluminum bisulfate, potassium alum, ammonium alum, sodium alum, and sodium aluminate.

Further, in view of solubility with an aqueous solution to be absorbed, the polyvalent metal salt is more preferably water-soluble polyvalent metal salt with water of crystallization.

The polyvalent metal salt may be used in the singular, or two or more of the polyvalent metal salts may be used in combination.

The polyvalent metal salt used in the present invention is particularly preferably aluminum sulfate, aluminum sulfate 18-hydrate and aluminum sulfate 14-hydrate to 18-hydrate.

The amount of the polyvalent metal salt included in the water-absorbing agent of the present invention is preferably 0.001 to 10 mass % and more preferably 0.01 to 5 mass % on the polyvalent metal salt basis with respect to the water-absorbing agent. The amount is preferably 0.0001 to 2 mass % and more preferably 0.001 to 1 mass % on polyvalent metal basis (cation basis) with respect to the water-absorbing agent.

When the amount of the polyvalent metal salt included in the water-absorbing agent is 0.001 mass % or more, it is possible to obtain a water-absorbing agent with high Saline Flow Conductivity (SFC). When the amount is 10 mass % or less, it is possible to suppress a decrease in Centrifuge Retention Capacity (CRC), which is preferable.

It is preferable that the polyvalent metal salt in the present invention is mixed, in the form of an aqueous solution, with the water-absorbent resin. In this case, the concentration of the polyvalent metal salt preferably ranges from 30 mass % to saturated concentration in view of mixing property and an increase in SFC. When the concentration of the polyvalent metal salt is 30 mass % or more, it is possible to suppress permeation of the polyvalent metal salt into the water-absorbent resin, enabling even mixture, and it is possible to increase SFC. Further, the concentration of the polyvalent metal salt is preferably the saturated concentration or less since it is possible to suppress generation of dust particles caused by deposition of salt.

(1-4) Other Components

The water-absorbing agent of the present invention includes the water-absorbent resin particles as a main component and includes (i) the compound that includes a constitutional unit derived from polyalkyleneglycol and that is other than an unsaturated monomer and (ii) the polyvalent metal salt, as essential components. Further, the water-absorbing agent may include other component if necessary.

An example of the other component is water and/or other additive. The other component is to be included in such an amount that does not impair water absorption properties. The amount of the other component is preferably 3 mass % or less. Further, the amount of water to be included is preferably approximately 2 mass %. When the other component is included in the water-absorbing agent, various properties are given to the water-absorbing agent.

Examples of the other additive include water-soluble polycation compounds such as polyethyleneimine, polyvinylamine, and polyallylamine; water-insoluble inorganic fine particles such as silica, alumina, and bentonite; odor eliminating agent; antibacterial agent; perfume; expanding agent; pigment; dye; elasticizer; adhesive; surfactant; oxidizer; reducing agent; salt; chelator; fungicide; paraffin; hydrophobic macromolecule; thermoplastic resin such as polyethylene and polypropylene; and thermosetting resin such as polyester resin and urea resin. The water-absorbing agent may include such additive if necessary in a range that does not drop water absorption properties of the water-absorbing agent such as liquid-permeability, e.g. in a range of approximately 0 to 10 mass % with respect to the water-absorbent resin particles.

(1-5) Properties of the Water-Absorbing Agent of the Present Invention

The water-absorbing agent of the present invention has Centrifuge Retention Capacity (CRC) ranging from 5 to 20 g/g, preferably from 10 to 20 g/g, and more preferably from 12 to 18 g/g. CRC is an index of ability to absorb and to retain an aqueous solution.

By nature, the water-absorbing agent has high ability to absorb and to retain an aqueous solution. However, a fiber material used in an absorbent core has high ability to let an aqueous solution to permeate, but has relatively low ability to retain an aqueous solution. For that reason, in order to attain the ability of the fiber material used in the absorbent core, the water-absorbing agent of the present invention preferably has CRC in a range from 5 to 20 g/g.

Conventionally, CRC has been desired to have a high value such as 30 g/g or more and 40 g/g or more. By setting CRC of the water-absorbing agent to be low, i.e. 5 to 20 g/g, the water-absorbing agent can be preferably used in place of the fiber material in the absorbent core. In particular, it is confirmed from FIG. 4 that the relation between CRC and SFC is increased greatly in the range from 12 to 18 g/g.

When CRC is lower than 5 g/g, the amount of used water-absorbing agent increases, which may make it difficult to make sanitary materials such as diapers thinner. When CRC is higher than 20 g/g, there is a possibility of low liquid-permeability.

In addition to having CRC ranging from 5 to 20 g/g, the water-absorbing agent of the present invention includes the compound that includes a constitutional unit derived from polyalkyleneglycol and that is other than an unsaturated monomer and polyvalent metal salt, thereby realizing excellent SFC. Consequently, it is possible to provide a water-absorbing agent that has an improved relation between CRC and SFC and that has high SFC in a range of CRC being 20 g/g or less.

SFC of the water-absorbing agent of the present invention is preferably 400 $cm^3 \cdot s \cdot 10^{-7}/g$ or more, more preferably 600 $cm^3 \cdot s \cdot 10^{-7}/g$ or more, and still more preferably 800 $cm^3 \cdot s \cdot 10^{-7}/g$ or more. The upper limit of SFC of the water-absorbing agent is not particularly limited, and it is preferably 4000 $cm^3 \cdot s \cdot 10^{-7}/g$ or less and more preferably 3000 $cm^3 \cdot s \cdot 10^{-7}/g$ or less.

SFC is an index of ability of liquid-permeability among swollen gels under pressure. When SFC is in the above range, an aqueous solution is allowed to diffuse quickly in a longitudinal direction or a lateral direction after the water-absorbing agent absorbs the aqueous solution. When SFC is lower than 400 $cm^3 \cdot s \cdot 10^{-7}/g$, an aqueous solution does not diffuse sufficiently in an absorbent core, which may cause leakage of the aqueous solution.

As described above, the water-absorbing agent of the present invention has CRC ranging from 5 to 20 g/g and SFC of 400 $cm^3 \cdot s \cdot 10^{-7}/g$ or more, and the two properties are compatible in a good balance. Accordingly, it is possible to provide a water-absorbing agent that can be used in place of the fiber material used for sanitary materials such as diapers.

The solid content of the water-absorbing agent of the present invention ranges preferably from 80 to 99.9 mass %, more preferably from 85 to 99 mass %, and still more preferably from 90 to 98 mass %. The solid content being 80 mass % or more is preferable since it ensures high handleability of the water-absorbing agent and high CRC. The solid content being less than 80 mass % is not preferable since CRC drops.

The shape of the water-absorbing agent of the present invention is not particularly limited as long as the shape allows the water-absorbing agent to satisfy the above properties. The shape is preferably a particulate shape, but may be a sheet shape or a fiber shape for example.

In a case where the water-absorbing agent used in the present invention has a particulate shape, a particle diameter and a particle diameter distribution of the water-absorbing agent is not particularly limited. In order to further enhance the effect of the present invention, mass average particle diameter (D50) ranges preferably from 100 to 850 µm, more preferably from 200 to 600 µm, still more preferably from 250 to 550 µm, and particularly preferably from 300 to 500 µm. Further, logarithmic standard deviation ($\sigma\xi$) ranges preferably from 0.1 to 0.6, more preferably from 0.2 to 0.5, and still more preferably from 0.25 to 0.4. Smaller logarithmic standard deviation ($\sigma\xi$) of particle diameter distribution indicates narrower particle diameter distribution. In the water-absorbent resin particles and the water-absorbing agent of the present invention, it is important that the particle diameter distribution is not only narrow but also has a width to some extent. When logarithmic standard deviation ($\sigma\xi$) is less than 0.1, there is a possibility that a desired ability cannot be obtained and productivity drops greatly. When logarithmic standard deviation ($\sigma\xi$) is more than 0.6, the particle diameter distribution is too broad and there is a possibility that a desired ability cannot be obtained.

In the water-absorbent resin particles and the water-absorbing agent of the present invention, examples of a preferable combination of mass average particle diameter (D50) and logarithmic standard deviation ($\sigma\xi$) of particle diameter distribution include: a combination of mass average particle diameter (D50) of not less than 300 µm and less than 400 µm and logarithmic standard deviation ($\sigma\xi$) of particle diameter distribution ranging from 0.25 to 0.4 (mass average particle diameter is small and a range of particle diameter distribution is narrow); and a combination of mass average particle diameter (D50) ranging from 400 µm to 500 µm and logarithmic standard deviation ($\sigma\xi$) of particle diameter distribution ranging from 0.25 to 0.4 (mass average particle diameter is large and a range of particle diameter distribution is narrow).

In the case where the water-absorbing agent of the present invention has a particulate shape, in order to further enhance the effect of the present invention, the water-absorbing agent preferably includes 90 to 99.99 mass % of particles with 1000 to 45 µm in particle diameter. The water-absorbing agent more preferably includes 90 to 99.99 mass % and still more preferably includes 95 to 99.99 mass % of particles with 850 to 106 µm in particle diameter. The water-absorbing agent still more preferably includes 90 to 99.99 mass % and particularly preferably 95 to 99.99 mass % of particles with 850 to 150 µm in particle diameter. When there are many particles with less than 150 µm in particle diameter, there is a possibility that liquid-permeability becomes low and accordingly the effect of the present invention is not sufficiently exerted. When there are many particles with more than 850 µm in particle diameter, there is a possibility that a human body feels an uncomfortable sensation when touching the particles in actual use.

The water-absorbing agent of the present invention has two compatible properties in a good balance: Centrifuge Retention Capacity (CRC) and Saline Flow Conductivity (SFC). Therefore, the water-absorbing agent is preferably applicable to sanitary materials such as diapers, incontinence pads, sanitary napkins, and tampons; water-absorbing agent for portable toilet; solidifying agent for waste solution; and water retaining agent for agriculture. In particular, the water-absorbing agent of the present invention is applicable to sanitary materials such as diapers.

(2) Method for Producing Water-Absorbing Agent of the Present Invention

The method for producing water-absorbing agent of the present invention is not particularly limited as long as it is a method for producing a water-absorbing agent that includes water-absorbent resin particles obtained by polymerizing an acid group-containing unsaturated monomer, that has CRC ranging from 5 to 20 g/g, and that includes (i) a compound that includes a constitutional unit derived from polyalkyleneglycol and that is other than an unsaturated monomer and (ii) polyvalent metal salt.

The method for producing the water-absorbing agent of the present invention includes the steps of:

(2-1) (A) producing a crosslinked polymer hydrogel by polymerizing an acid group-containing unsaturated monomer in the presence of an internal crosslinking agent;

(2-2) (B) obtaining water-absorbent resin particles (not surface-crosslinked) by drying the crosslinked polymer hydrogel obtained in the step (A); and (2-3) (C) obtaining surface-crosslinked water-absorbent resin particles by surface crosslinking the water-absorbent resin particles (not surface-crosslinked) obtained in the step (B), and the method further includes at least the steps of:

(2-4) adding the compound that includes a constitutional unit derived from polyalkyleneglycol and that is other than an unsaturated monomer to a monomer or the water-absorbent resin particles; and (2-5) adding polyvalent metal salt to the water-absorbent resin particles.

In the method for producing the water-absorbing agent of the present invention, it is particularly preferable that the step of adding the compound that includes a constitutional unit derived from polyalkyleneglycol and that is other than an unsaturated monomer is performed before the step (A) or in the step (A). The step of adding the compound that includes a constitutional unit derived from polyalkyleneglycol and that is other than an unsaturated monomer may be performed before, at the same time with, or after adding a surface crosslinking agent and before heating in the step (C). This provides a water-absorbing agent that has an improved relation between Centrifuge Retention Capacity (CRC) and Saline Flow Conductivity (SFC) and high SFC in a range of CRC being 20 g/g or less.

Further, in the method for producing the water-absorbing agent of the present invention, it is preferable that the step of adding polyvalent metal salt is performed in the step (C) or after the step (C). This yields the effect of increasing SFC. The following sequentially explains the steps.

(2-1) Step (A)

In this step, an acid group-containing unsaturated monomer is polymerized in the presence of an internal crosslinking agent to obtain a crosslinked polymer hydrogel. For the step of polymerizing the acid group-containing unsaturated monomer, aqueous solution polymerization or reversed-phase suspension polymerization is generally carried out in consideration of the performance or easiness in controlling the polymerization. These polymerization methods can be carried out in an air atmosphere. The polymerization methods are more preferably carried out in an atmosphere of an inert gas such as nitrogen or argon (e.g. 1% oxygen or oxygen lower than 1%). For that reason, for example, a monomer component is used for polymerization after oxygen dissolved therein has sufficiently been displaced with the inert gas (e.g. oxygen lower than 1 ppm).

The aqueous solution polymerization is preferably used in the method for producing the water-absorbing agent of the present invention. Examples of particularly preferable aqueous solution polymerization include continuous belt polymerization and continuous or batch kneader polymerization. The method disclosed in U.S. Pat. No. 6,906,159 for example is a preferable polymerization method, too.

The reversed-phase suspension polymerization is a polymerization method in which the aqueous monomer solution is suspended into a hydrophobic organic solvent, and examples thereof are disclosed in U.S. Patents such as U.S. Pat. No. 4,093,776, U.S. Pat. No. 4,367,323, U.S. Pat. No. 4,446,261, U.S. Pat. No. 4,683,274, and U.S. Pat. No. 5,244,735. The aqueous solution polymerization is a polymerization method in which an aqueous monomer solution is polymerized without using any dispersion solvent, and examples thereof are disclosed in U.S. Patents such as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808, and in European patents such as EP 0811636, EP 0955086, EP 0922717, and EP 1178059. Monomers, crosslinking agents, polymerization initiators, and other additives which are described in the patent documents listed above are applicable to the present invention.

In a case where the aqueous solution polymerization or the reversed-phase suspension polymerization is carried out in the method for producing the water-absorbing agent of the present invention, the acid group-containing unsaturated monomer is used as an aqueous solution including at least an internal crosslinking agent if necessary (hereinafter referred to as a monomer aqueous solution in the present specification). Therefore, the method for producing the water-absorbing agent of the present invention may further include the step of preparing a monomer aqueous solution including the acid group-containing unsaturated monomer and the one or more internal crosslinking agents.

The acid group-containing unsaturated monomer and the internal crosslinking agent used in this step have been already explained in the (1-1) and therefore the explanations thereof are omitted here.

Further, in the step (A), in combination with the acid group-containing unsaturated monomer, other monomer described in the item (1-1) may be copolymerized if necessary. In a case where other monomer is copolymerized, the monomer aqueous solution includes not only the acid group-containing unsaturated monomer but also the other monomer. Hereinafter, the monomer included in the monomer aqueous solution is merely referred to as a monomer. The monomer included in the monomer aqueous solution is, in the case (a) the other monomer is not used, an acid group-containing unsaturated monomer, and in the case (b) the other monomer is used, the acid group-containing unsaturated monomer and the other monomer.

In view of physical properties, the concentration of the monomer in the monomer aqueous solution ranges preferably from 10 to 70 mass %, more preferably from 15 to 65 mass %, still more preferably from 30 to 65 mass %, particularly preferably from 30 to 60 mass %, and most preferably from 35 to 55 mass %. A solvent other than water may be used in combination if necessary. The kind of the solvent other than water is not particularly limited.

A preferable example of the method for producing the water-absorbing agent of the present invention is such that, in the step (A), the compound that includes a constitutional unit derived from polyalkyleneglycol and that is other than an unsaturated monomer is prepared to have the above amount and is mixed with the monomer aqueous solution at the time of polymerization. The monomer aqueous solution at the time of polymerization is not limited to the monomer aqueous solution before polymerization, and includes a monomer aqueous solution during polymerization and a gel including the monomer aqueous solution. The compound is added one or more times at a stage where a degree of polymerization of the monomer is 0 to 99 mol %, preferably 0 to 70 mol %, and more preferably 0 to 50 mol %.

In particular, in a case where the compound that includes a constitutional unit derived from polyalkyleneglycol and that is other than an unsaturated monomer is mixed with the monomer aqueous solution in the method of the present invention, the compound may be mixed at any timing before and after putting a polymerization initiator, and the timing of mixing and the method for mixing are not particularly limited, but it is preferable that the compound is added in a monomer aqueous solution before polymerization (degree of polymerization is 0%). Therefore, it is preferable that mixture of the compound that includes a constitutional unit derived from polyalkyleneglycol and that is other than an unsaturated monomer is carried out in the step of preparing a monomer aqueous solution.

A polymerization initiator, a water-soluble resin, a water-absorbent resin, an expanding agent, a surfactant or the like may be added to the monomer aqueous solution.

Examples of the water-soluble resin and the water-absorbent resin include starch, polyacrylic acid (salt), and polyethyleneimine. The water-soluble resin and the water-absorbent resin may be added to the monomer in a range of, for example, 0 to 50 mass %, preferably 0 to 20 mass %, and more preferably 0 to 10 mass % with respect to the monomer. Examples of the expanding agent include carbonate, azo compound, and air bubble. The expanding agent may be added to the monomer in a range of, for example, 0 to 5 mol %, and preferably 0 to 1 mass % with respect to the monomer.

If necessary, the acid group-containing unsaturated monomer may be neutralized with a basic substance in the step of preparing a monomer aqueous solution.

It is preferable that raw materials for the water-absorbing agent (such as acid group-containing unsaturated monomer, other monomer, internal crosslinking agent, and compound that includes a constitutional unit derived from polyalkyleneglycol and that is other than an unsaturated monomer) is a water-soluble compound. In the present invention, "water-soluble compound" means a compound whose solubility to 100 ml of ion-exchanged water at normal pressure and at $25 \pm 2°$ C. is essentially 1 g or more, preferably 5 g or more, and more preferably 10 g or more.

In view of physical properties, the amount of the internal crosslinking agent in use is 0.001 to 3 mol %, more preferably 0.01 to 2 mol %, and still more preferably 0.02 to 1 mol % with respect to the monomer.

The internal crosslinking agent may be used in the singular or two or more internal crosslinking agents may be used in combination. In a case where a plurality of internal crosslinking agents are used, ratios of individual crosslinking agents are not particularly limited.

It is further preferable that for the water-absorbent resin of the present invention, an internal crosslinking agent including four or more functional groups each capable of forming a covalent bond with an acid group and an internal crosslinking agent with two or more polymerizable ethylenic double bonds are used together. This ensures a further increase in liquid-permeability of the obtained water-absorbent resin and the obtained water-absorbing agent.

In this case, a ratio of the internal crosslinking agent including four or more functional groups each capable of forming a covalent bond with an acid group to the internal crosslinking agent with two or more polymerizable ethylenic double bonds, i.e., a ratio of the amount of a used internal crosslinking agent including four or more functional groups each capable of forming a covalent bond with an acid group to the amount of a used internal crosslinking agent with two or more polymerizable ethylenic double bonds, preferably ranges from 90:10 to 10:90 in a molar ratio.

The internal crosslinking agent is required to exist at a time of polymerization of a monomer, and may be added before the polymerization of a monomer or in the course of the polymerization. The internal crosslinking agent may be added to a reaction system at one time or several times. In a case where at least one internal crosslinking agent is used, in consideration of water absorption property etc. of the water-absorbent resin particles or the water-absorbing agent that is an end product, it is preferable that an internal crosslinking agent with two or more polymerizable ethylenic double bonds is used in polymerization. In a case where the internal crosslinking agent is solely an internal crosslinking agent forming a covalent bond, internal crosslinking is caused by heating in a drying step or a surface crosslinking step that will be mentioned later. In a case where the internal crosslinking agent is an internal crosslinking agent with two or more polymerizable ethylenic double bonds, internal crosslinking is caused in the polymerization step.

In the step (A), the acid group-containing unsaturated monomer may be polymerized in the presence of a particular amount of a polymerization inhibitor as well as the internal crosslinking agent. The polymerization inhibitor is preferably methoxyphenols, more preferably p-methoxyphenol. The amount of used methoxyphenols ranges from 10 to 200 mass ppm, preferably from 10 to 90 mass ppm, and particularly preferably from 20 to 90 mass ppm.

In the method for producing the water-absorbing agent of the present invention, the acid group-containing unsaturated monomer is used after being neutralized with a basic substance if necessary. The basic substance used for neutralization is preferably hydroxide of alkali metal, such as sodium hydroxide, potassium hydroxide, and lithium hydroxide, and particularly preferably sodium hydroxide. The neutralization may be performed for a monomer before polymerization, for a polymer in the course of polymerization or after polymerization, or for both the monomer and the polymer.

When the monomer aqueous solution is polymerized, a radical polymerization initiator such as persulfate (e.g. potassium persulfate, ammonium persulfate, and sodium persulfate), t-buthylhydroperoxide, hydrogen peroxide, 2,2'-azobis(2-amidinopropane)dihydrochloride, 2-hydroxy-1-phenyl-propane-1-one, and benzoinmethylether may be used. In the case of using the radical polymerization initiator, a reducing agent for promoting decomposition of the radical polymerization initiator, such as sodium sulfite, sodium hydrogen sulfite, ferrous sulfate, and L-ascorbic acid may be used in combination with the radical polymerization initiator, and the combination of the reducing agent and the radical polymerization initiator may serve as a redox initiator. The amounts of the reducing agent and the radical polymerization initiator in use ranges from generally 0.00001 to 0.2 mol % and further from 0.0001 to 0.1 mol % with respect to the monomer.

Instead of using the polymerization initiator, an active energy ray such as radioactive ray, electron beam, and ultraviolet ray may be irradiated to a reaction system to carry out polymerization. An active energy ray such as radioactive ray, electron beam, and ultraviolet ray may be used in combination with the polymerization initiator.

In polymerization, 0 to 30 mass % of hydrophilic macromolecule such as starch-cellulose, starch-cellulose derivative, polyvinylalcohol, polyacryllic acid (salt), and crosslinked polyacryllic acid (salt) may be added to whole monomers (water-soluble monomers other than internal crosslinking agent), or 0 to 1 mass % of a chain transfer agent such as hypophosphite may be added to whole monomers (water-soluble monomers other than internal crosslinking agent).

The reaction temperature and time in the above polymerization reaction is not particularly limited and may appropriately be set according to factors such as the kind of the acid group-containing unsaturated monomer. However, the polymerization is usually carried out at not higher than the boiling point preferably within 3 hours, more preferably within 1 hour, still more preferably within 0.5 hour, and at a peak temperature of preferably not higher than 150° C., more preferably in the range of 80 to 130° C. In addition, it is also preferable that water and/or acrylic acid as vaporized during the polymerization is, if necessary, collected and then recycled to the step of producing the water-absorbent resin.

<Crushing of Crosslinked Polymer Hydrogel>

In general, the crosslinked polymer hydrogel (it may hereinafter abbreviated as hydrogel in the present specification) produced in the step (A) is crushed into pieces with a size suitable for drying, and then subjected to steps such as drying, pulverization, classification, and surface crosslinking, resulting in a water-absorbing agent.

Examples of a method for crushing a crosslinked polymer hydrogel include: a continuous kneader polymerization or batch kneader polymerization in which polymerization is carried out while crushing a crosslinked polymer hydrogel produced in a reaction receptacle with crushing means; and continuous belt polymerization in which polymerization is carried out without crushing and then a crosslinked polymer hydrogel is crushed by a crushing device or the like; and a combination of both methods.

Therefore, depending on the kind of the polymerization method, the crosslinked polymer hydrogel may be dried directly, or if necessary, the crosslinked polymer hydrogel is crushed by the crushed device etc. In view of physical properties, the temperature of hydrogel in crushing is kept or heated to be in a range preferably from 40 to 95° C., and more preferably from 50 to 80° C.

Solid content of resin of the hydrogel is not particularly limited. In view of physical properties, the solid content ranges preferably from 10 to 70 mass %, more preferably from 15 to 65 mass %, and still more preferably from 30 to 60 mass %.

As described above, in the case of the continuous kneader polymerization or the batch kneader polymerization, the hydrogel is crushed during polymerization. In the case of the continuous belt polymerization, the hydrogel is crushed after polymerization. For example, using a device for carrying out the extrusion pulverization as a crushing device, hydrogel can be extruded from a multi-pore structure with 0.3 to 30 mm, more preferably 5 to 30 mm, still more preferably 5 to 20 mm in pore diameter and be crushed. Examples of the shape of a pore include: a circle; a quadrangle such as a square and a rectangle; a triangle; and a hexagon, and the shape is not particularly limited. Preferable shape is a circle. The pore diameter is defined by a diameter obtained by converting a perimeter of an opening into a perimeter of a circle.

When the pore diameter of the multi-pore structure is less than 0.3 mm, there is a possibility that the hydrogel has a string shape or cannot be extruded from the pore. When the pore diameter of the multi-pore structure is more than 30 mm, the hydrogel is not sufficiently dried, resulting in a possibility that the effect of the present invention cannot be exerted.

Examples of the device for carrying out the extrusion pulverization include a screw type and a rotating roll type, each of which can press-feed the hydrogel from its supply port to a multi-pore plate. The screw type extruder may have a single axis or plural axes, and may be one generally used for extrusion molding of meat, rubber and plastic, and may be one used as a crushing device. For example, a meat chopper or a dome gran may be used.

In this case, water, polyhydric alcohol described in the above listing of an internal crosslinking agent, a mixture solution of water and the polyhydric alcohol, an aqueous solution in which the polyvalent metal in the above listing of an internal crosslinking agent is solved, and vapor thereof, may be added.

As a preferable example of the method for producing the water-absorbing agent of the present invention, the compound that includes a constitutional unit derived from polyalkyleneglycol and that is other than an unsaturated monomer may be mixed at a time of crushing the hydrogel.

(2-2) Step (B)

In this step, the crosslinked polymer hydrogel obtained in the step (A) is dried to obtain water-absorbent resin particles (not surface-crosslinked). That is, the crosslinked polymer hydrogel obtained in the step (A) is dried and, if necessary, pulverized, classified, and granulated, and is then surface-crosslinked.

The condition under which the crosslinked polymer hydrogel is dried is not particularly limited. The crosslinked polymer hydrogel is dried at a range, in general, from 150° C. to 250° C., preferably from 150° C. to 220° C., more preferably from 160° C. to 200° C., and still more preferably from 180° C. to 200° C. When the crosslinked polymer hydrogel is dried at less than 150° C., internal crosslinking reaction is less likely to occur or much amount of undried products remain, which drops productivity. When the crosslinked polymer hydrogel is dried at more than 250° C., there is a possibility that the resulting water-absorbent resin gets colored. In a case where oil or vapor is used as a heating medium, the drying temperature is defined by a temperature of the heat medium. In a case where drying is carried out without using the heat medium, e.g. an electron beam is irradiated, the drying temperature is defined by a temperature of a material (material to be dried). Further, the drying temperature may change gradually. The drying time depends on a surface area of a hydrous polymer, water content of the hydrous polymer, and the kind of a drying device, and is selected so as to obtain desired water content. The drying time may range from 10 to 180 minutes for example, and preferably ranges from 30 to 120 minutes. Further, the drying method described in U.S. Pat. No. 4,920,202 specification may be used.

The crosslinked polymer hydrogel is dried to have solid content ranging preferably from 70 to 99.8 mass %, more preferably from 80 to 99.7 mass %, and still more preferably from 90 to 99.5 mass %. When the solid content after drying is out of this range, the increase in physical properties caused by surface treatment (crosslinking) of the water-absorbent resin particles is difficult. Finally, the water-absorbing agent with solid content ranging from 90 to 99.5 mass % can be obtained.

Examples of usable drying methods include various methods such as: heat-drying; hot-air drying; vacuum drying; infrared drying; microwave drying; dehydration by azeotropy with hydrophobic organic solvents; and high-moisture drying by high-temperature steaming. Various methods are usable to obtain desired water content, and are not particularly limited.

In this step, pulverization is carried out before and/or after the drying step, preferably after the drying step, and thereafter the water-absorbent resin particles (not surface-crosslinked) are obtained.

The condition under which the crosslinked polymer hydrogel (crushed product) is pulverized, preferably after being dried, is not particularly limited. Conventionally known pulverizers such as a roll mill and a hammer mill may be used. The shape resulting from the pulverization is preferably an irregularly pulverized shape, and more preferably partially including particles with wide surface area and granulated shape.

The water-absorbent resin particles usable in the present invention are classified for example so that mass average particle diameter ranges preferably from 100 to 850 µm, more preferably from 200 to 600 µm, and still more preferably from 250 to 550 µm, and particularly preferably from 300 to 500 µm. Further, logarithmic standard deviation (σξ) is set to be in a range preferably from 0.1 to 0.6, more preferably from 0.2 to 0.5, and still more preferably from 0.25 to 0.4. By setting the mass average particle diameter (D50) and the logarithmic standard deviation (σξ) of the water-absorbent resin particles of the present invention in this way, it is possible to further exert the effect of the present invention.

In a case where classification is carried out according to necessity in the present invention, it is necessary to select a sieve for the classification in consideration of classification efficiency. For example, in a case where water-absorbent resin particles having passed through a sieve having mesh opening size of 150 µm are removed through classification, it is difficult to completely remove particles with a particle diameter of 150 µm or less. Therefore, it is desirable to suitably select a usable sieve in order to obtain water-absorbent resin particles or a water-absorbing agent with a desired particle diameter.

In order to further exert the effect of the present invention, the water-absorbent resin particles usable in the present invention preferably include 90 to 99.9 mass % of particles with particle diameter of 1000 to 45 µm. The water-absorbent resin particles preferably include 90 to 99.9 mass %, and more preferably include 95 to 99.9 mass %, of particles with particle diameter of 850 to 106 µm. Further, the water-absorbent resin particles still more preferably include 90 to 100 mass %, and particularly preferably include 95 to 100 mass %, of particles with particle diameter of 850 to 150 µm. When much amount of particles with particle diameter of less than 150 µm exist, liquid-permeability drops, resulting in a possibility that the effect of the present invention is not sufficiently exerted. When much amount of particles with particle diameter of more than 850 µm exist, there is a possibility that a human body feels an uncomfortable sensation when touching the particles in actual use.

(2-5) Step (C)

In order to further exert the effect of the present invention, it is preferable that the method for producing the water-absorbing agent of the present invention produces surface-crosslinked water-absorbent resin particles obtained by surface crosslinking the water-absorbent resin particles (not surface-crosslinked) obtained in the step (B).

The surface crosslinking agent usable in this step has been already explained in the aforementioned item (1-1) and therefore the explanation thereof will be omitted here. Such surface crosslinking agent may be used in the singular or two or more of them may be used in combination. Among them, it is more preferable to use a surface crosslinking agent capable of forming a covalent bond with a functional group (carboxyl group) on the surface of the water-absorbent resin particles since such surface crosslinking agent increases absorption properties against pressure. Further, polyhydric alcohol is preferable since it is highly safe and increases hydrophilicity on the surface of the water-absorbent resin particles. Further, use of the polyhydric alcohol enhances the affinity of the surfaces of the water-absorbent resin particles to the polyvalent metal particles, and interaction between residue of the polyhydric alcohol and the surface of the polyvalent metal allows the polyvalent metal particles to exist more evenly on the surface of the water-absorbent resin particles.

The quantity of the surface crosslinking agent as used depends upon factors such as the types of the compounds used and combinations thereof, but is preferably in the range of 0.001 to 10 parts by weight, more preferably 0.01 to 5 parts by weight, with respect to 100 parts by weight of the water-absorbent resin particles (water-absorbent resin particles that are not surface-crosslinked).

Water may be used for mixing the surface crosslinking agent and the water-absorbent resin particles (water-absorbent resin particles that are not surface-crosslinked). The quantity of water, as used on this occasion, is usually in the range of preferably 0.1 to 10 parts by weight, more preferably 0.5 to 5 parts by weight, with respect to 100 parts by weight of the solid content of the water-absorbent resin particles.

A hydrophilic organic solvent may be used as a mixing auxiliary agent in mixing the surface crosslinking agent or an aqueous solution thereof with the water-absorbent resin particles (not surface-crosslinked).

The quantity of the hydrophilic organic solvent, as used on this occasion, depends on factors such as the kind of the water-absorbent resin particles, particle diameter, and water content, but is in the range of preferably 0 to 10 parts by weight, more preferably 0 to 5 parts by weight, and still more preferably 0 to 3 parts by weight, with respect to 100 parts by weight of the solid content of the water-absorbent resin particles. The temperature of the crosslinking agent solution is preferably set in the range of 0° C. to boiling point, more preferably 5 to 50° C., still more preferably 10 to 30° C., in terms of the mixability and stability. In addition, the temperature of the water-absorbent resin before the mixture is preferably in the range of 0 to 80° C., more preferably 40 to 70° C., in terms of the mixability. Further, the additive described in U.S. Pat. Nos. 5,610,208 and 5,610,220 may be used.

Furthermore, in the present invention, one preferred mixing method is a method including the steps of premixing the surface crosslinking agent with water and/or the hydrophilic organic solvent, if necessary, and then spraying or dropwise adding (more preferably, spraying) the resultant aqueous solution to the water-absorbent resin to mix them together. The size of the liquid droplets as sprayed averages preferably 1 to 300 μm, more preferably 10 to 200 μm. In addition, in the mixing step, there may be allowed to coexist water-insoluble fine-particulate powder and/or surfactants within the range not damaging the effects of the present invention, for example, within the range of 0 to 10 mass %, preferably 0 to 5 mass %, more preferably 0 to 1 mass %, with respect to the water-absorbent resin. The surfactants as used and their quantities are exemplified in the International Publication WO2005/75070 (international filing date: Feb. 4, 2005).

A preferable mixing apparatus as used for the aforementioned mixing step needs to be able to generate great mixing power to ensure homogeneous mixing. Various mixing machines are usable in the present invention, but preferably they are high-speed agitation type mixers, particularly preferably, high-speed agitation type continuous mixers. Examples of such mixers are Turbulizer (product name; produced by Hosokawa Micron Corporation of Japan) and Lödige Mixer (product name; produced by Gebruder Lödige Maschinenbau GmbH of Germany).

After mixing with the surface crosslinking agent, the resulting water-absorbent resin particles are preferably subjected to a heating treatment. The heating treatment is preferably carried out under the conditions where the heating temperature is preferably in the range of 120 to 250° C., more preferably 150 to 250° C. The heating time is preferably in the range of 1 minute to 2 hours. The heating treatment can be carried out by using conventional dryers or heating-furnaces. Examples of the dryers include channel type blending dryers, rotary dryers, disk dryers, fluidized-bed dryers, gas blowing type dryers, and infrared dryers. In addition, after being heated, the water-absorbent resin may be cooled, if necessary.

These surface crosslinking methods are also disclosed in: various European patents such as European Patent Nos. 0349240, 0605150, 0450923, 0812873, 0450924, and 0668080; various Japanese patent documents such as Japanese Unexamined Patent Publication Nos. 242709/1995 and 224304/1995; various U.S. patents such as U.S. Pat. Nos. 5,409,771, 5,597,873, 5,385,983, 5,610,220, 5,633,316, 5,674,633, and 5462972; and various international patent publications such as WO 99/42494, WO 99/43720, and WO 99/42496. These surface crosslinking methods are also applicable to the present invention.

(2-4) Step of Adding the Compound that Includes a Constitutional Unit Derived from Polyalkyleneglycol and that is Other than an Unsaturated Monomer In the method for producing the water-absorbing agent of the present invention, the step of adding the compound that includes a constitutional unit derived from polyalkyleneglycol and that is other than an unsaturated monomer is preferably performed before or in the step (A). Further, the step of adding the compound that includes a constitutional unit derived from polyalkyleneglycol and that is other than an unsaturated monomer may be performed before, at the same time with, or after addition of the surface crosslinking agent in the step (C) and before the heating.

A preferable example of the method for producing the water-absorbing agent of the present invention is such that the compound that includes a constitutional unit derived from polyalkyleneglycol and that is other than an unsaturated monomer is prepared to have the amount and mixed with the monomer aqueous solution at the time of polymerization in the step (A). The monomer aqueous solution at the time of polymerization is not limited to a monomer aqueous solution before the polymerization, but includes a monomer aqueous solution during the polymerization or a gel including the monomer aqueous solution. The compound that includes a constitutional unit derived from polyalkyleneglycol and that is other than an unsaturated monomer is added at least one time at a stage where a degree of polymerization of a monomer ranges from 0 to 99 mol %, more preferably from 0 to 70 mol %, and particularly preferably from 0 to 50 mol %.

In the case of mixing, in the monomer aqueous solution, the compound that includes a constitutional unit derived from polyalkyleneglycol and that is other than an unsaturated monomer as an example of the method of the present invention, the compound may be mixed at any timing before and after putting the polymerization initiator. The timing and method for the mixing is not particularly limited. It is preferable to add the compound to a monomer aqueous solution before polymerization (degree of polymerization 0%). Therefore, it is preferable that the compound that includes a constitutional unit derived from polyalkyleneglycol and that is other than an unsaturated monomer is mixed in the step of preparing the monomer aqueous solution.

Further, as a preferable example of the method for producing the water-absorbing agent of the present invention, the compound that includes a constitutional unit derived from polyalkyleneglycol and that is other than an unsaturated monomer may be mixed at a time when a hydrogel is crushed.

Addition of the compound that includes a constitutional unit derived from polyalkyleneglycol and that is other than an unsaturated monomer may be performed through a method suitably selected from a method of directly adding the compound and a method of adding the compound as a solution, an aqueous solution, or an aqueous liquid for uniform addition, according to the state of an object to which the compound is to be added. In the case of adding the compound as a solution, an aqueous solution, or an aqueous liquid, the concentration of the solution etc. may range substantially from 1 to 50 mass %. If necessary, a surfactant etc. may be added. A solvent is evaporated according to necessity.

(2-5) Step of Adding Polyvalent Metal Salt

In the method for producing the water-absorbing agent of the present invention, it is preferable that the step of adding polyvalent metal salt is performed in or after the step (C) in order to further exert the effect of the present invention.

It is more preferable that the polyvalent metal salt is added in the surface crosslinking and before the heating, e.g. concurrently with the surface crosslinking agent. Further, it is particularly preferable that the polyvalent metal salt is added after the step of surface crosslinking and separately from the step of surface crosslinking.

This allows a resulting water-absorbing agent to have high Saline Flow Conductivity (SFC).

The amount of usable polyvalent metal salt and the method of adding the polyvalent metal salt have been already explained in the item (1-3) and therefore explanations thereof are omitted here.

Furthermore, in the step of adding the polyvalent metal salt, the solvent may be evaporated if necessary after addition of the polyvalent metal salt.

EXAMPLES

Hereinafter, the present invention will be explained according to Examples below. However, the present invention is not limited to descriptions of Examples. In addition, the properties (a) to (g) described in the specification including the claims and Examples of the present invention, were determined by the following measurement methods. In a case where the measurements are described as to a water-absorbing agent, the same measurement can be made for water-absorbent resin particles by replacing the water-absorbing agent with the water-absorbent resin particles.

(a) Mass Average Particle Diameter (D50) and Logarithmic Standard Deviation (σξ) of Particle Diameter Distribution Water-absorbent resin particles or a water-absorbing agent was riddled by JIS standard sieves with mesh openings being 850 μm, 710 μm, 600 μm, 500 μm, 425 μm, 300 μm, 212 μm, 150 μm, 45 μm etc., and percentage R of the residues was plotted on a logarithmic probability paper. Thus, particle diameter corresponding to R=50 mass % was read as mass average particle diameter (D50). Further, logarithmic standard deviation (σξ) of particle diameter distribution is represented by Equation 1 and smaller σξ means narrower particle diameter distribution.

$$\sigma\xi = 0.5 \times \ln(X2/X1) \quad \text{Equations 1}$$

(where X1 is particle diameter at a time R=84.1% and X2 is particle diameter at a time R=15.9%)

Classification at a time of measuring mass average particle diameter (D50) and logarithmic standard deviation (σξ) of particle diameter distribution was performed as follows: 10.0 g of water-absorbent resin particles or a water-absorbing agent was put in the JIS standard sieves (IIDA TESTING SIEVE: diameter 8 cm) with mesh openings being 850 μm, 710 μm, 600 μm, 500 μm, 425 μm, 300 μm, 212 μm, 150 μm, 45 μm etc., and was classified for 5 minutes by a vibrating classifier (IIDA SIEVE SHAKER, TYPE: ES-65 (rotational frequency: 60 Hz 230 rpm, number of concussion: 60 Hz 130 rpm), SER. No. 0501) under conditions that the temperature was a room temperature (23±2° C.) and humidity was 50 RH %.

(b) Centrifuge Retention Capacity (CRC)

Centrifuge Retention Capacity (CRC) means absorption capacity for 0.90 mass % aqueous sodium chloride solution (i.e. physiological saline) with no pressure for 30 minutes. CRC also referred to as absorption capacity without load.

0.200 g of water-absorbent resin particles or a water-absorbing agent was evenly put in a bag (60 mm×85 mm) made of unwoven fabric (produced by Nangoku Pulp Kogyo K.K., product name: heatron paper, type: GSP-22) and was heat-sealed, and was then immersed in 0.90 mass % aqueous sodium chloride solution (physiological saline) with an excessive amount (in general, substantially 500 ml) at 23 (±2) ° C. The bag was drawn up after 30 minutes, the bag was drained of water by a centrifuge (produced by KOKU-SAN Co. Ltd., type: H-122) for 3 minutes with a centrifugal force (250G) described in edana ABSORBENCY II 441.1-99, and then the weight $W_1$ (g) of the bag was measured. Furthermore, the same operation was performed without the water-absorbent resin particles or the water-absorbing agent, the weight $W_0$ (g) of the bag at that time was measured, and Centrifuge Retention Capacity (CRC) (g/g) was calculated based on Equation 2.

$$\text{CRC(g/g)} = (W_1(g) - W_0(g))/(\text{mass(g) of water-absorbent resin particles or water-absorbing agent})) - 1 \quad \text{Equation 2}$$

(c) Solid Content

Solid content indicates a ratio of a component that does not evaporate at 180° C. to the water-absorbing agent. A relation between the solid content and water content is as follows.

Solid content(mass %)=100−water content(mass %)

The solid content was measured as follows.

Approximately 1 g of a water-absorbing agent (mass $W_1$) was put in an aluminum cup (mass $W_0$) with a bottom diameter being approximately 5 cm, and left still in a windless drier at 180° C. for 3 hours so that the water-absorbing agent is dried. The weight of aluminum cup+the water-absorbing agent ($W_2$) after the drying was measured, and the solid content was measured based on Equation 3.

$$\text{solid content(mass \%)} = ((W_2 - W_0)/W_1) \times 100 \quad \text{Equation 3}$$

(d) Saline Flow Conductivity (SFC)
(SFC Measurement Device)

Saline Flow Conductivity (SFC) of a gel layer formed in a water-absorbing agent that had absorbed physiological saline and had been swollen under load was measured.

Darcy's Law and a steady flow method are used for measurement of Saline Flow Conductivity (SFC) (see "Absorbency", edited by P. K. Chatterjee, Elsevier, 1985, pages 42-43, and Chemical Engineering Vol. II, third edition, J. M. Coulson and J. F. Richarson, Pergamon Press, 1978, pages 125-127 for example).

FIG. 1 illustrates a device suitable for the measurement. The device includes a storage tank (202) with approximately 5 L in capacity, placed on a labo jack (203). The storage tank (202) includes a glass tube with an open end and a rubber plug section (200), each for a function for keeping the height of the still water to be certain. By pulling out a rubber plug section (201), it is possible to add a solution to the storage tank (202). The storage tank (202) has a solution exit provided under a solution surface in the storage tank (202), and a glass tube (204) with a valve (205) is connected with the storage tank (202). Flow of the solution is controlled by opening/closing the valve (205). The glass tube (204) is connected with a flexible tube (210). The other end of the flexible tube (210) is provided so as to flow the solution to an SFC device (206) shown as a whole. The SFC device (206) is provided on a supporter (209) having a stainless wire mesh with a mesh opening of 1 mm. A collection tank (207) for collecting the solution is provided under the supporter (209). The collection tank (207) is provided on a scale (208). The scale (208) is connected with a computer so that the amount of the collected solution is recorded per a certain time.

In FIG. 1, for convenience of understanding FIG. 1, devices at the right side (such as the SFC device 206, the collection tank 207, the scale 208, and the supporter 209) are illustrated in an enlarged size compared with the devices at the left side.

Figure 2:
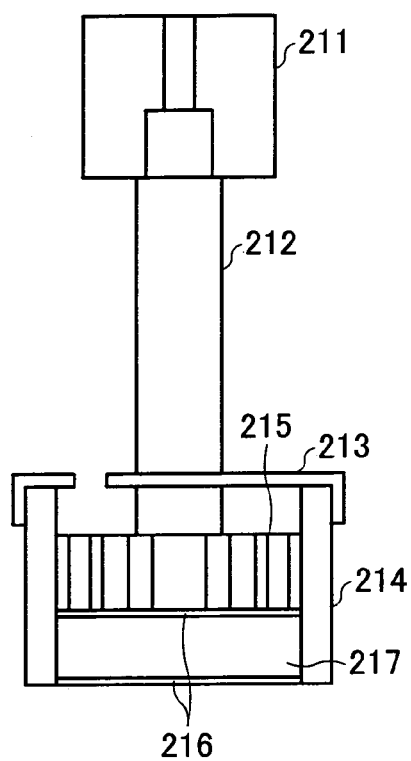
FIG. 2 is a cross sectional view schematically illustrating a part of the measurement device used for measuring SFC.
Figure 3:
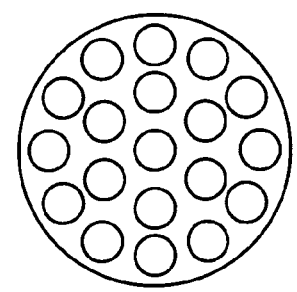
FIG. 3 is a bottom view illustrating a piston head of the measurement device used for measuring SFC.

As illustrated in FIG. 2, the SFC device basically includes: a cylinder (214) with a stainless wiremesh at its bottom (obtained by modifying LEXANR or similar product); a piston (212) (obtained by modifying LEXANR or similar product); a cover (213) (obtained by modifying LEXANR or similar product) with an orifice to which a tube for flowing the solution is inserted; and a weight (211). As illustrated in FIG. 3, the piston (212) includes a piston head (215) with holes. As illustrated in FIG. 3, each of the holes of the piston head (215) has a cylindrical structure that penetrates the piston head (215) in a vertical direction. A wiremesh (216) with 400 meshes (mesh opening: 38 μm) (produced by Weisse & Eschrich, material: SUS304, mesh width: 0.038 mm, wire diameter: 0.025 mm) is attached to a lower surface of the piston head (215). The piston head (215) has a diameter a little smaller than the internal diameter of the cylinder (214) and has a size that allows the piston head (215) to move sliding inside the cylinder (214)

in a vertical direction without any disturbance. An upper part of the shaft of the piston (212) is fabricated so that the weight can be placed on the upper part. The cylinder (214) has an internal diameter of 6.00 cm (bottom area: 28.27 cm$^2$), a wall thickness of 0.5 cm; and a height of 6.0 cm. A wiremesh (216) with 400 meshes (mesh opening: 38 μm) (produced by Weisse & Eschrich, material: SUS304, mesh width: 0.038 mm, wire diameter: 0.025 mm) is attached to a bottom of the cylinder (214). The cover (213) has a hole a little wider than an outline of the shaft, and has a size that allows the piston (212) to move sliding in the shaft in a vertical direction without any disturbance. Furthermore, the cover (213) has an orifice to which the tube for flowing the solution is inserted. The weight consisting of the weights of the weight (211) and the piston (212) is adjusted to be 2.07 kPa (0.3 psi) with respect to the bottom surface of the cylinder.

(SFC Measurement Method)

First, the height ($h_0$: unit is mm and effective digits are four) and the weight ($W_0$: unit is g and effective digits are four) of the SFC device consisting of the cylinder (214) before a water-absorbing agent being put therein, i.e. in a hollow state; the piston (212); the cover (213); and the weight (211) were measured. Next, 3.00±0.05 g of a water-absorbing agent was weighed out (W: unit is g and effective digits are four). It is preferable that the amount of the weighed water-absorbing agent is adjusted so that d final as explained later ranges from 10 mm to 20 mm and it is more preferable that the amount is adjusted so that d final ranges from 15 mm to 20 mm. For example, in a case where absorption capacity without load (CRC) ranges from 5 g/g to 16 g/g, the amount of the water-absorbing agent is 3.00±0.05 g, in a case where CRC is more than 16 g/g and not more than 20 g/g, the amount of the water-absorbing agent is 2.00±0.03 g, and in a case where CRC is more than 20 g/g and not more than 25 g/g, the amount of the water-absorbing agent is 1.60±0.03 g, and in a case where CRC is more than 25 g/g and not more than 30 g/g, the amount of the water-absorbing agent is 1.30±0.03 g. It is preferable that the amount of the water-absorbing agent to be weighed out is adjusted so that d final as explained later is in the above range. The weighed water-absorbing agent was put on the whole bottom surface of the cylinder (214) so as to be dispersed carefully and evenly. After the water-absorbing agent was put, the piston (212), the cover (213), and the weight (211) were provided, and the height ($h_1$: unit is mm) of the SFC device was measured. Next, saline (0.9 mass % sodium chloride aqueous solution) was poured in a petri dish with 16 cm or more in diameter and 4 cm or more in height so that the SFC device was immersed in the saline from the bottom up to at least 3 cm. A filter paper (produced by ADVANTEC: No. 2) with 90 mm in diameter was placed on an internal bottom surface of the petri dish. The SFC device in which the water-absorbing agent was put was placed on the filter paper and the water-absorbing agent was caused to be swollen for 60 minutes. After 60 minutes, the SFC device was taken out of the petri dish, and the height ($h_2$: unit was mm and effective digits were four) and the weight ($W_2$: unit was g and effective digits were four) of the SFC device after the water-absorbing agent had been swollen was measured. Thereafter, the SFC device was moved to and put on the supporter (209) of an SFC measurement device, and the flexible tube (210) was provided at the orifice. Next, the valve (205) was open so as to flow the solution. After starting the flow of the solution, before the amount of the solution that flowed through the gel layer and was collected reached approximately 200 g as displayed by the scale, an adjustment was made so that the height of still water in the cylinder kept to be 5 cm. This adjustment may be performed by adjusting the height of the labo jack (203) or by adjusting the height of the lower part of the glass tube inserted from the upper part of the storage tank 202. At a time when the height of the still water in the cylinder was adjusted to keep being 5 cm, the computer connected with the scale started acquiring data indicative of the weight of the solution having been through the gel layer and been collected. Acquisition of the data was performed per 5 sec and until 180 sec. However, when the amount of collected solution reached 2 kg or more after starting the acquisition of the data and before 180 sec, the acquisition of the data was stopped at the time (e.g. 120 sec). On the other hand, when the amount of the collected solution reached 100 g or less at 180 sec after starting the acquisition of the data, the acquisition of the data was prolonged to 600 sec, and after ending the acquisition of the data, the valve (205) was closed promptly. After closing the valve (205), the height ($h_3$: unit was mm and effective digits were four) of the SFC device was measured at a time when the solution that poured from the lower part of the cylinder (214) of the SFC device substantially stopped (at a time when the height of the still water surface in the cylinder (214) corresponded to the height of the gel layer). Thereafter, the SFC device was moved onto a cylindrical device with the same internal diameter as that of the cylinder (214), and drip-off was made for 30 minutes. The SFC device was put onto the cylindrical device so that drip-off was properly carried out while the surface right under the wiremesh on which the water-absorbing agent was provided in the cylinder did not touch anything. After the drip-off for 30 minutes, the height ($h_4$: unit was mm and effective digits were four) and the weight ($W_4$: unit was g and effective digits were four) of the SFC device were measured.

(Calculation of SFC)

Time t (sec) acquired by the computer and weight (g) of the collected solution were plotted on a graph as an X-axis and a Y-axis, respectively. The plot was subjected to linear approximation by least square method, and an inclination (rate: unit g/s) of the line was obtained.

SFC was obtained through the following equation.

$$\text{SFC}(\text{cm}^3 \cdot \text{s} \cdot 10^{-7}/\text{g}) = (d\text{ final} \times \text{rate})/(\text{Area} \times \text{Density} \times \text{Pressure}) \times 10000000$$

where Area (cm$^2$)=28.27, Density (g/cm$^3$)=1.005 (density of saline at 20° C. is used), d final (cm)={($h_2-h_0$)+($h_3-h_0$)}/2/10

(e) Molecular Weight and Elution Weight of Polyethyleneglycol (PEG) Having Eluted from Water-Absorbent Resin Particles and Water-Absorbing Agent 1000 g of ultra pure water (specific resistance was 1.5MΩ·cm or more) was poured into a covered plastic receptacle of 1 litter in capacity, 1.00 g of water-absorbent resin or a water-absorbing agent was put in the aqueous solution, the resulting solution was stirred by Teflon® stirrer tip (length 35 mm, thickness (diameter of cross section perpendicular to a longitudinal direction) 7 mm, stick-like shape) at 600 rpm for 16 hours, so that water-soluble component of the water-absorbent resin particles or the water-absorbing agent was extracted. The extract solution was filtered by a filter paper (ADVANTEC Toyo Kaisha, Ltd., product name: JIS P 3801, No. 2, thickness 0.26 mm, diameter of captured particles 5 μm) with use of a Buchner funnel to obtain a resultant filtrate, and the whole amount of the resultant filtrate was put in an eggplant-shaped flask with 1 litter in capacity, and water was evaporated at 60° C. by an evaporater (produced by Yamato Scientific Co., Ltd., product name: Rotary Evaporator RE50). Next, 10.0 ml of an eluant as explained below was poured in the eggplant-shaped flask from which water had evaporated, the internal side of the flask was washed well (dried and condensed objects were dissolved), and the resulting solution was filtered by a filter with 0.45 µm (product name: chromato disc, 25A, hydrophilic 0.45 µm, produced by GL Sciences Inc.), so that a GPC (gel permeation chromatography) measurement sample was obtained. The sample was measured under the following GPC measurement conditions, and the molecular weight and the elution weight of PEG having eluted was calculated using a calibration curve as presented below.

<GPC Measurement Conditions>

Eluant: aqueous solution obtained by dissolving $NaH_2PO_4.2H_2O$ and $Na_2HPO_4.12H_2O$ in ultra pure water so that concentration of $NaH_2PO_4.2H_2O$ is 60 mM and concentration of $Na_2HPO_4.12H_2O$ is 20 mM.

Standard sample: 0.005 g of Poly(ethylene glycol) Standard purchased from Polymer Standards Service GmbH ((i) Mw=330, (ii) Mw=600, (iii) Mw=1000, (iv) Mw=2000, (v) Mw=6000, (vi) Mw=11000, (vii) Mw=23000) was dissolved in 10.0 ml of eluant and subjected to GPC measurement so as to form a calibration curve.

GPC system: SHODEX GPC-SYSTEM-21

Guard column: SHODEX Asahipak GF-1G7B (produced by Showa Denko K.K.)

Sample column: Two TOSOH GMPWXLs directly connected with each other (produced by Tosoh Corporation)

Column temperature: 35° C. (constant)

Flow rate: 0.5 ml/min

UV detector: wavelength 205 nm (f) Extractable Polymer Content

Into a covered plastic receptacle of 250 ml in capacity, 184.3 g of saline was weighed out. Then, 1.00 g of water-absorbing agent was added to this aqueous solution, and they were stirred for 16 hours, and thus soluble components were extracted from the resin. The resultant extract liquid was filtrated with a filter paper (produced by ADVANTEC Toyo Co., Ltd., product name: (JIS P 3801, No. 2), thickness: 0.26 mm, diameter of captured particles: 5 µm), and then 50.0 g of the resultant filtrate was weighed out and used as a measuring solution.

To begin with, only the saline was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was carried out also for the measuring solution, thus obtaining titration amounts ([NaOH] ml and [HCl] ml).

For example, in a case of a water-absorbing agent including acrylic acid and its sodium salt in known amounts, the extractable polymer content of the water-absorbing agent was calculated from the average molecular weight of the monomers and the titration amounts obtained from the above procedures, in accordance with Equation 4 as presented below.

Extractable polymer content(wt %)=0.1×(average molecular weight)×184.3×100×([HCl]−[bHCl])/ 1000/1.0/50.0  Equation 4

In the case of unknown amounts, the average molecular weight of the monomers was calculated from the neutralization ratio (Equation 5 as presented below) determined by the titration.

Neutralization ratio(mol %)=[1−([NaOH]−[bNaOH])/ ([HCl]−[bHCl])]×100  Equation 5

(g) Content of Polyvalent Metal Salt Included in Water-Absorbing Agent (on Polyvalent Metal Basis (Cationic Basis))

Into a polypropylene beaker of 260 ml in capacity, 1.0 g of a water-absorbing agent was weighed out, 190.0 g of saline (0.9 wt % NaCl aqueous solution) and 10.0 g of 2N hydrochloric acid were added, and the resulting solution was stirred at a room temperature for 30 minutes. After the stirring, the supernatant fluid was filtered by a chromato disc (GL chromato disc 25A, produced by GL Sciences Inc.), and the resultant filtrate was analyzed with plasma emission spectrometry (produced by HORIBA Ltd., ULTIMA) to obtain concentration of polyvalent metal component.

The calibration curve was made based on saline including polyvalent metal component in a known amount. Based on the obtained concentration of polyvalent metal component, content (on polyvalent metal basis (cation basis)) of polyvalent metal salt included in the water-absorbing agent is represented by the following equation.

Content(on polyvalent metal basis(cation basis)) of polyvalent metal salt included in water-absorbing agent(wt %)=(concentration of polyvalent metal component in solution (wt %))×200  Equation 5

Example 1

In a polypropylene receptacle of 1 liter in capacity, a solution (A) was prepared by mixing 373.14 g of acrylic acid, 8.11 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 309.92 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution. 4.50 g of polyethylene glycol 6000 (average molecular weight 6000, produced by KANTO CHEMICAL CO., INC.) was added to the monomer aqueous solution (C) while stirring the monomer aqueous solution (C), thus a monomer aqueous solution (D) was obtained.

Subsequently, at a time when the temperature of the monomer aqueous solution (D) dropped to 97° C., 13.81 g of 3 mass % sodium persulfate aqueous solution was added to the monomer aqueous solution (D) while stirring the monomer aqueous solution (D), and the resulting solution was poured, in an open system, into a stainless bat-shaped receptacle with Teflon® coated inside, that was heated by a hot plate (NEO HOTPLATE H1-1000, produced by IUCHI SEIEIDO CO., LTD.) to have a surface temperature of 100° C. The stainless bat-shaped receptacle has a shape such that the area of the bottom surface is 250×250 mm, the area of the upper surface is 640×640 mm, the height is 50 mm, the central cross section is a trapezoid, and the upper surface is open.

Polymerization started soon after the polymer aqueous solution (D) to which the sodium persulfate aqueous solution had been added was poured into the stainless bat-shaped receptacle. The polymerization proceeded with production of vapor and expansion and effervescence both in vertical and lateral directions, and then the resulting crosslinked polymer hydrogel (hydrogel) contracted to a size a little larger than the bottom surface. The expansion and the contraction ended within approximately 1 minute. The resulting crosslinked polymer hydrogel (hydrogel) was kept in the polymerization receptacle (stainless bat-shaped receptacle) for 3 minutes, and then the crosslinked polymer hydrogel (hydrogel) was taken out. These procedures were carried out in a system open to the air.

The resulting crosslinked polymer hydrogel (hydrogel) was crushed by a meat chopper (MEAT-CHOPPER TYPE: 12VR-400KSOX, produced by Iizuka Kogyo Co., Ltd., die pore diameter: 6.4 mm, number of pores: 38, die thickness: 8 mm) and thus the crosslinked polymer hydrogel was crushed into pieces (crushed products were obtained). At that time, the crosslinked polymer hydrogel was put in an amount of approximately 350 g/min, and crushing was carried out while deionized water was added in an amount of approximately 80 g/min concurrently with the putting of the crosslinked polymer hydrogel.

The crosslinked polymer hydrogel crushed into pieces (crushed products) was spread over a stainless mesh with mesh opening of 850 μm, and was dried with heated wind at 180° C. for 30 minutes. The resulting dried products were pulverized by a roll mill (WML type roll pulverizer, produced by Inoguchi Giken, Ltd.) and classified by a JIS standard sieve with mesh openings of 850 μm and 45 μm, so that irregularly pulverized water-absorbent resin particles with solid content being 96 mass %, mass average particle diameter (D50) being 465 μm, and logarithmic standard deviation (σξ) of particle diameter distribution being 0.36 was obtained.

A surface crosslinking agent solution made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution was mixed were subjected to a heating treatment by a hot drier (temperature: 180° C.) for 1 hour and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained.

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propyleneglycol was added to 100 parts by mass of the surface-crosslinked water-absorbent resin particles. After the addition, the resultant was dried at 60° C. for 1 hour without wind, and the resulting particles were caused to pass the JIS standard sieve with mesh opening of 850 μm, so that a water-absorbing agent (1) was obtained. Table 1 shows properties of the water-absorbing agent (1). Particle diameter distribution of the water-absorbing agent is substantially the same as that of the water-absorbent resin particles.

Example 2

In a polypropylene receptacle of 1 litter in capacity, a solution (A) was prepared by mixing 373.14 g of acrylic acid, 1.49 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 314.66 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution. 4.50 g of polyethylene glycol 6000 (average molecular weight 6000, produced by KANTO CHEMICAL CO., INC.) and 1.89 g of D-sorbitol were added to the monomer aqueous solution (C) while stirring the monomer aqueous solution (C), thus a monomer aqueous solution (D) was obtained.

Subsequently, polymerization, drying, pulverization, and classification were carried out in the same way as Example 1, so that irregularly pulverized water-absorbent resin particles with solid content being 95 mass %, mass average particle diameter (D50) being 461 μm, and logarithmic standard deviation (σξ) of particle diameter distribution being 0.34 was obtained.

A surface crosslinking agent made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 75 minutes and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained.

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propyleneglycol was added to 100 parts by mass of the surface-crosslinked water-absorbent resin particles. After the addition, the resultant was dried at 60° C. for 1 hour without wind, and the resulting particles were caused to pass the JIS standard sieve with mesh opening of 850 μm, so that a water-absorbing agent (2) was obtained. Table 1 shows properties of the water-absorbing agent (2). Particle diameter distribution of the water-absorbing agent is substantially the same as that of the water-absorbent resin particles.

Furthermore, a reference water-absorbing agent (1) was obtained by carrying out the same procedures as Example 2 except that a time for the heating treatment for surface crosslinking of the water-absorbent resin particles was 45 minutes. CRC of the reference water-absorbing agent (1) was 18.6 (g/g), SFC of the reference water-absorbing agent (1) was 457 ($cm^3 \cdot s \cdot 10^{-7}$/g), which was high SFC for the water-absorbing agent with CRC being approximately 18 (g/g) in general.

Example 3

In a reactor made by attaching a lid to a jacketed stainless-steel twin-arm kneader of 10 liters in capacity equipped with two sigma type blades, 578.1 g of acrylic acid, 4235.0 g of 37 mass % acrylic acid sodium aqueous solution, 605.0 g of deionized water, 7.10 g of polyethylene glycol diacrylate (molecular weight 523), 8.99 g of D-sorbitol (produced by Wako Pure Chemical Industries, Ltd.), and 21.45 g of polyethylene glycol 6000 (average molecular weight 6000, produced by KANTO CHEMICAL CO., INC.) were dissolved, so that a reaction solution was obtained.

Subsequently, the reaction solution was deaerated in nitrogen gas atmosphere for 20 minutes while being adjusted to have a temperature of 25° C. Then, 19.7 g of 15 mass % sodium persulfate aqueous solution and 24.7 g of 0.1 mass % L-ascorbic acid aqueous solution were added to the reaction solution while stirring the reaction solution, and after 30 seconds polymerization started. The temperature at which the polymerization started was 25.2° C.

While crushing a resulting gel, polymerization was carried out at 25 to 95° C., and at 30 minutes after the polymerization had started, a crosslinked polymer hydrogel was taken out. The crosslinked polymer hydrogel had a particle diameter of approximately 10 mm or less.

The crosslinked polymer hydrogel crushed into pieces was spread over a stainless mesh with mesh opening of 850 μm, and was dried with heated wind at 180° C. for 45 minutes. The resulting dried products were pulverized by a roll mill (WML type roll pulverizer, produced by Inoguchi Giken, Ltd.) and classified by a JIS standard sieve with mesh openings of 850 μm and 45 μm, so that irregularly pulverized water-absorbent resin particles with solid content being 95 mass %, mass average particle diameter (D50) being 465 μm, and logarithmic standard deviation (σξ) of particle diameter distribution being 0.34 was obtained.

A surface crosslinking agent made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 1 hour and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained.

A mixture solution made by mixing 0.80 parts by mass of aluminum sulfate 27 mass % aqueous solution (8 wt % on aluminum oxide basis), 0.134 parts by mass of sodium lactate 60 mass % aqueous solution, and 0.016 parts by mass of propyleneglycol was added to 100 parts by mass of the surface-crosslinked water-absorbent resin particles. After the addition, the resultant was dried at 60° C. for 1 hour without wind, and the resulting particles were caused to pass the JIS standard sieve with mesh opening of 850 μm, so that a water-absorbing agent (3) was obtained. Table 1 shows properties of the water-absorbing agent (3). Particle diameter distribution of the water-absorbing agent was substantially the same as that of the water-absorbent resin particles.

Furthermore, measurement of molecular weight and elution weight of polyethyleneglycol having eluted from the water-absorbing agent (3) shows that the molecular weight of eluted polyethyleneglycol was the same as the used polyethyleneglycol 6000 and the elution weight of the polyethyleneglycol occupied much of the used polyethyleneglycol 6000 (90% or more of the used polyethyleneglycol 6000).

Example 4

A water-absorbing agent (4) was obtained in the same way as Example 2 except that the amount of deionized water in the solution (B) was 318.71 g, the amount of polyethylene glycol 6000 (average molecular weight 6000, produced by KANTO CHEMICAL CO., INC.) added to the monomer aqueous solution (C) was 0.45 g, and the time for the heating treatment for surface crosslinking water-absorbent resin particles was 1 hour. Table 1 shows properties of the water-absorbing agent (4).

Example 5

100 parts by mass of the surface-crosslinked water-absorbent resin particles obtained in Example 4 were heated to have a temperature of 150° C., and 1.6 parts by mass of potassium alum (potassium aluminum sulfate 12 hydrate) was evenly mixed with the surface-crosslinked water-absorbent resin particles for 5 minutes while stirring the water absorbent resin particles, so that a water-absorbing agent (5) was obtained. Table 1 shows properties of the water-absorbing agent (5).

Example 6

A water-absorbing agent (6) was obtained in the same way as Example 2 except that the amount of deionized water in the solution (B) was 301.11 g, the amount of polyethylene glycol 6000 (average molecular weight 6000, produced by KANTO CHEMICAL CO., INC.) added to the monomer aqueous solution (C) was 18.00 g, and the time for the heating treatment for surface crosslinking water-absorbent resin particles was 75 minutes. Table 1 shows properties of the water-absorbing agent (6).

Example 7

A water-absorbing agent (7) was obtained in the same way as Example 2 except that the amount of deionized water in the solution (B) was 316.91 g, polyethylene glycol 6000 (average molecular weight 6000, produced by KANTO CHEMICAL CO., INC.) added to the monomer aqueous solution (C) was replaced with 2.25 g of polyethyleneglycol 1000 (average molecular weight 1000, produced by Wako Pure Chemical Industries, Ltd.), and the time for the heating treatment for surface crosslinking water-absorbent resin particles was 1 hour. Table 1 shows properties of the water-absorbing agent (7).

Example 8

A water-absorbing agent (8) was obtained in the same way as Example 7 except that polyethylene glycol 1000 (average molecular weight 1000, produced by Wako Pure Chemical Industries, Ltd.) added to the monomer aqueous solution (C) was replaced with polyethyleneglycol 2000 (average molecular weight 2000, produced by Wako Pure Chemical Industries, Ltd.). Table 1 shows properties of the water-absorbing agent (8).

Furthermore, a reference water-absorbing agent (2) was obtained in the same way as Example 7 except that polyethylene glycol 1000 (average molecular weight 1000, produced by Wako Pure Chemical Industries, Ltd.) added to the monomer aqueous solution (C) was replaced with polyethyleneglycol 20000 (average molecular weight 20000, produced by Wako Pure Chemical Industries, Ltd.). CRC of the reference water-absorbing agent (2) was 17.0 (g/g), SFC of the reference water-absorbing agent (2) was 566 (cm³·s·

$10^{-7}$/g), which was high SFC for the water-absorbing agent with CRC being approximately 17 (g/g) in general.

Example 9

A water-absorbing agent (9) was obtained in the same way as Example 7 except that polyethylene glycol 1000 (average molecular weight 1000, produced by Wako Pure Chemical Industries, Ltd.) added to the monomer aqueous solution (C) was replaced with polyethyleneglycol monostearate (product name: EMANON 3199V, produced by Kao Corporation). Table 1 shows properties of the water-absorbing agent (9).

Example 10

In a polypropylene receptacle of 1 litter in capacity, a solution (A) was prepared by mixing 373.14 g of acrylic acid, 1.49 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 319.16 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 101° C. due to heat of neutralization and heat of dissolution. 1.89 g of D-sorbitol was added to the monomer aqueous solution (C) while stirring the monomer aqueous solution (C), thus a monomer aqueous solution (D) was obtained.

Subsequently, polymerization, drying, pulverization, and classification were carried out in the same way as Example 1, so that irregularly pulverized water-absorbent resin particles with solid content being 96 mass %, mass average particle diameter (D50) being 465 µm, and logarithmic standard deviation (σξ) of particle diameter distribution being 0.36 was obtained.

A surface crosslinking agent solution made by mixing 0.48 parts by mass of 1, 4 butanediol, 0.75 parts by mass of propylene glycol, 4.0 parts by mass of deionized water, and 0.5 parts by mass of polyethylene glycol 6000 (average molecular weight 6000, produced by KANTO CHEMICAL CO., INC.) was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 1 hour and surface crosslinking was carried out. After the heating treatment, the resulting water-absorbent resin particles were crushed so that the particles passed a JIS standard sieve with mesh opening of 850 µm. Thus, surface-crosslinked water-absorbent resin particles were obtained.

A mixture solution made by mixing 0.80 parts by mass of aluminum sulfate 27 mass % aqueous solution (8 wt % on aluminum oxide basis), 0.134 parts by mass of sodium lactate 60 mass % aqueous solution, and 0.016 parts by mass of propyleneglycol was added to 100 parts by mass of the surface-crosslinked water-absorbent resin particles. After the addition, the resultant was dried at 60° C. for 1 hour without wind, and the resulting particles were caused to pass the JIS standard sieve with mesh opening of 850 µm, so that a water-absorbing agent (10) was obtained. Table 1 shows properties of the water-absorbing agent (10). Particle diameter distribution of the water-absorbing agent was substantially the same as that of the water-absorbent resin particles.

Example 11

Example 11 was arranged so that the surface crosslinking agent solution in Example 10 was replaced with a mixture solution made by mixing 0.48 parts by mass of 1, 4 butanediol, 0.75 parts by mass of propylene glycol, 3.4 parts by mass of deionized water, 0.5 parts by mass of polyethylene glycol 6000 (average molecular weight 6000, produced by KANTO CHEMICAL CO., INC.), and 0.80 parts by mass of aluminum sulfate 27 mass % aqueous solution (8 mass % on aluminum oxide basis), and the mixture solution was evenly sprayed to and mixed with 100 parts by mass of the water-absorbent resin particles while stirring the 100 parts by mass of the water-absorbent resin particles, and the heating treatment and the surface crosslinking were carried out. After the heating treatment, the resulting water-absorbent resin particles were crushed so that the particles passed the JIS standard sieve with mesh opening of 850 µm, thus a surface-crosslinked water-absorbing agent (11) was obtained. Table 1 shows properties of the water-absorbing agent (11).

Reference Example 12

A water-absorbing agent (12) was obtained in the same way as Example 7 except that 2.25 g of polyethylene glycol 1000 (average molecular weight 1000, produced by Wako Pure Chemical Industries, Ltd.) added to the monomer aqueous solution (C) was replaced with 4.50 g of polyethyleneglycol 600 (average molecular weight 600, produced by Wako Pure Chemical Industries, Ltd.). Table 1 shows properties of the water-absorbing agent (12).

Comparative Example 1

In a polypropylene receptacle of 1 litter in capacity, a solution (A) was prepared by mixing 373.14 g of acrylic acid, 8.11 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 309.92 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution.

Subsequently, at a time when the temperature of the monomer aqueous solution (C) dropped to 97° C., 13.81 g of 3 mass % sodium persulfate aqueous solution was added to the monomer aqueous solution (C) while stirring the monomer aqueous solution (C), and the resulting solution was poured, in an open system, into a stainless bat-shaped receptacle with Teflon® coated inside, that was heated by a hot plate (NEO HOTPLATE H1-1000, produced by IUCHI SEIEIDO CO., LTD.) to have a surface temperature of 100° C. The stainless bat-shaped receptacle has a shape such that the area of the bottom surface is 250×250 mm, the area of the upper surface is 640×640 mm, the height is 50 mm, the central cross section is a trapezoid, and the upper surface is open.

Polymerization started soon after the monomer aqueous solution (C) to which the sodium persulfate aqueous solution had been added was poured into the stainless bat-shaped receptacle. The polymerization proceeded with production of vapor and expansion and effervescence both in vertical and lateral directions, and then the resulting crosslinked polymer hydrogel (hydrogel) contracted to a size a little larger than the bottom surface. The expansion and the contraction ended within approximately 1 minute. The resulting crosslinked polymer hydrogel (hydrogel) was kept in the polymerization receptacle (stainless bat-shaped receptacle) for 3 minutes, and then the crosslinked polymer hydrogel (hydrogel) was taken out. These procedures were carried out in a system open to the air.

The resulting crosslinked polymer hydrogel (hydrogel) was crushed by a meat chopper (MEAT-CHOPPER TYPE: 12VR-400KSOX, produced by Iizuka Kogyo Co., Ltd., die pore diameter: 6.4 mm, number of pores: 38, die thickness: 8 mm) and thus the crosslinked polymer hydrogel was crushed into pieces (crushed products were obtained).

The crosslinked polymer hydrogel crushed into pieces (crushed products) was spread over a stainless mesh with mesh opening of 850 μm, and was dried with heated wind at 180° C. for 30 minutes. The resulting dried products were pulverized by a roll mill (WML type roll pulverizer, produced by Inoguchi Giken, Ltd.) and classified by a JIS standard sieve with mesh openings of 850 μm and 45 μm, so that irregularly pulverized water-absorbent resin particles with solid content being 96 mass %, mass average particle diameter (D50) being 463 μm, and logarithmic standard deviation (σξ) of particle diameter distribution being 0.35 was obtained.

A surface crosslinking agent solution made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 1 hour and surface crosslinking was carried out. After the heating treatment, the resulting water-absorbent resin particles were crushed so that the particles passed a JIS standard sieve with mesh opening of 850 μm. Thus, the surface-crosslinked water-absorbent resin particles were obtained. These water-absorbent resin particles were regarded as a comparative water-absorbing agent (1). Table 1 shows properties of the comparative water-absorbing agent (1).

Comparative Example 2

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propylene glycol was added to 100 parts by mass of the comparative water-absorbing agent (1). After the addition, the resultant was dried at 60° C. for 1 hour without any wind, and the resulting particles were caused to pass a JIS standard sieve with mesh opening of 850 μm, so that a comparative water-absorbing agent (2) was obtained. Table 1 shows properties of the comparative water-absorbing agent (2).

Comparative Example 3

In a reactor made by attaching a lid to a jacketed stainless-steel twin-arm kneader of 10 liters in capacity equipped with two sigma type blades, 578.1 g of acrylic acid, 4235.0 g of 37 mass % acrylic acid sodium aqueous solution, 626.4 g of deionized water, 7.10 g of polyethylene glycol diacrylate (molecular weight 523), and 8.99 g of D-sorbitol (produced by Wako Pure Chemical Industries, Ltd.), were dissolved, so that a reaction solution was obtained.

Subsequently, polymerization, drying, pulverization, and classification were carried out in the same way as Example 3, so that irregularly pulverized water-absorbent resin particles with solid content being 93 mass %, mass average particle diameter (D50) being 460 μm, and logarithmic standard deviation (σξ) of particle diameter distribution being 0.36 was obtained.

A surface crosslinking agent solution made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution was mixed were subjected to a heating treatment by a hot drier (temperature: 180° C.) for 1 hour and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained. The water-absorbent resin particles thus obtained were regarded as a comparative water-absorbing agent (3). Table 1 shows properties of the comparative water-absorbing agent (3).

Comparative Example 4

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propyleneglycol was added to 100 parts by mass of the comparative water-absorbing agent (3). After the addition, the resultant was dried at 60° C. for 1 hour without wind, and the resulting particles were caused to pass the JIS standard sieve with mesh opening of 850 μm, so that a comparative water-absorbing agent (4) was obtained. Table 1 shows properties of the comparative water-absorbing agent (4).

Comparative Example 5

The surface-crosslinked water-absorbent resin particles obtained in Example 2 (to which the mixture solution made of the aluminum sulfate aqueous solution, the sodium lactate aqueous solution, and the propylene glycol was not added) was regarded as a comparative water-absorbing agent (5). Table 1 shows properties of the comparative water-absorbing agent (5).

Comparative Example 6

The surface-crosslinked water-absorbent resin particles obtained in Example 10 (to which the mixture solution made of the aluminum sulfate aqueous solution, the sodium lactate aqueous solution, and the propylene glycol was not added) was regarded as a comparative water-absorbing agent (6). Table 1 shows properties of the comparative water-absorbing agent (6).

Comparative Example 7

In a polypropylene receptacle of 1 litter in capacity, a solution (A) was prepared by mixing 373.14 g of acrylic acid, 1.89 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 320.53 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained.

The monomer aqueous solution (C) raised its temperature up to 102° C. due to heat of neutralization and heat of dissolution. 0.11 g of 1,4-butanediol (produced by Wako Pure Chemical Industries, Ltd.) was added to the monomer aqueous solution (C) while stirring the monomer aqueous solution (C), thus a monomer aqueous solution (D) was obtained.

Subsequently, polymerization, drying, pulverization, and classification were carried out in the same way as Example 1, so that irregularly pulverized water-absorbent resin particles with solid content being 96 mass %, mass average particle diameter (D50) being 460 μm, and logarithmic standard deviation (σξ) of particle diameter distribution being 0.34 was obtained.

A surface crosslinking agent solution made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 75 minutes and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained. The water-absorbent resin particles thus obtained were regarded as a comparative water-absorbing agent (7). Table 1 shows properties of the comparative water-absorbing agent (7).

Comparative Example 8

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propylene glycol was added to 100 parts by mass of the comparative water-absorbing agent (7). After the addition, the resultant was dried at 60° C. for 1 hour without any wind, and the resulting particles were caused to pass a JIS standard sieve with mesh opening of 850 μm, so that a comparative water-absorbing agent (8) was obtained. Table 1 shows properties of the comparative water-absorbing agent (8).

Comparative Example 9

A comparative water-absorbing agent (9) was obtained in the same way as Comparative example 7 except that the amount of deionized water in the solution (B) was 316.03 g and 4.50 g of polyethylene glycol 6000 (average molecular weight 6000, KANTO CHEMICAL CO., LTD.) was added. Table 1 shows properties of the comparative water-absorbing agent (9).

Comparative Example 10

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propylene glycol were added to 100 parts by mass of the comparative water-absorbing agent (9). After the addition, the resultant was dried at 60° C. for 1 hour without any wind, and the resulting particles were caused to pass a JIS standard sieve with mesh opening of 850 μm, so that a comparative water-absorbing agent (10) was obtained. Table 1 shows properties of the comparative water-absorbing agent (10).

Comparative Example 11

In a polypropylene receptacle of 1 litter in capacity, a solution (A) was prepared by mixing 373.14 g of acrylic acid, 1.62 g of polyethylene glycol diacrylate (molecular weight 523), and 2.25 g of 1.0 mass % diethylenetriamine 5 acetic acid 3 sodium aqueous solution. Furthermore, a solution (B) was prepared by mixing 288.27 g of 48.5 mass % sodium hydroxide aqueous solution and 320.91 g of deionized water (ion-exchanged water) adjusted to have a temperature of 50° C. The solution (B) was quickly added to and mixed with the solution (A) while stirring the solution (A) with a magnetic stirrer, thus a monomer aqueous solution (C) was obtained. The monomer aqueous solution (C) raised its temperature up to 103° C. due to heat of neutralization and heat of dissolution.

Subsequently, polymerization, drying, pulverization, and classification were carried out in the same way as Example 1, so that irregularly pulverized water-absorbent resin particles with solid content being 94 mass %, mass average particle diameter (D50) being 466 μm, and logarithmic standard deviation (σξ) of particle diameter distribution being 0.33 was obtained.

A surface crosslinking agent solution made by mixing 0.48 parts by mass of 1, 4 butanediol, 0.75 parts by mass of propylene glycol, and 4.0 parts by mass of deionized water was evenly sprayed to and mixed with 100 parts by mass of the resulting water-absorbent resin particles while stirring the 100 parts by mass of the resulting water-absorbent resin particles. The water-absorbent resin particles with which the surface crosslinking agent solution had been mixed were subjected to a heating treatment by a hot drier (temperature: 180° C.) for 60 minutes and surface crosslinking was carried out. After the heating treatment, the resulting water-absorbent resin particles were crushed so that the particles passed a JIS standard sieve with mesh opening of 850 μm. Thus, surface-crosslinked water-absorbent resin particles were obtained. The water-absorbent resin particles thus obtained were regarded as a comparative water-absorbing agent (11). Table 1 shows properties of the comparative water-absorbing agent (11).

Comparative Example 12

A mixture solution made by mixing 0.80 parts by mass of aluminum sulfate 27 mass % aqueous solution (8 mass % on aluminum oxide basis), 0.134 parts by mass of sodium lactate 60 mass % aqueous solution, and 0.016 parts by mass of propylene glycol were added to 100 parts by mass of the comparative water-absorbing agent (11). After the addition, the resultant was dried at 60° C. for 1 hour without any wind, and the resulting particles were caused to pass a JIS standard sieve with mesh opening of 850 µm, so that a comparative water-absorbing agent (12) was obtained. Table 1 shows properties of the comparative water-absorbing agent (12).

Comparative Example 13

Surface-crosslinked water-absorbent resin particles were obtained in the same way as Comparative example 11 except that the amount of deionized water in the solution (B) was 318.66 g and 2.25 g of polyethylene glycol 6000 (average molecular weight 6000, KANTO CHEMICAL CO., LTD.) was added.

Subsequently, the resulting particles were caused to pass the JIS standard sieve with mesh opening of 850 µm, so that a comparative water-absorbing agent (13) was obtained. Table 1 shows properties of the comparative water-absorbing agent (13).

Comparative Example 14

A comparative water-absorbing agent (14) was obtained in the same way as Comparative example 11 except that the surface crosslinking agent solution used for surface crosslinking the water-absorbent resin particles in Comparative example 11 was replaced with a mixture solution made by mixing 0.48 parts by mass of 1, 4 butanediol, 0.75 parts by mass of propylene glycol, 4.0 parts by mass of deionized water, and 0.5 parts by mass of polyethylene glycol 6000 (average molecular weight 6000, produced by KANTO CHEMICAL CO., INC.). Table 1 shows properties of the comparative water-absorbing agent (14). Furthermore, a graph shown in FIG. 4 shows a relation between SFC and CRC obtained in Examples and Comparative examples.

TABLE 1

| | | compound including constitutional unit derived from polyalkyleneglycol | amount of added compound including constitutional structure derived from polyalkyleneglycol | addition of polyvalent metal salt | CRC | SFC |
|---|---|---|---|---|---|---|
| Example 1 | water-absorbing agent (1) | PEG6,000 | 1 wt % (added in polymerization) | added | 15.7 | 789 |
| Example 2 | water-absorbing agent (2) | PEG6,000 | 1 wt % (added in polymerization) | added | 13.7 | 1102 |
| Example 3 | water-absorbing agent (3) | PEG6,000 | 1 wt % (added in polymerization) | added | 16.2 | 824 |
| Example 4 | water-absorbing agent (4) | PEG6,000 | 0.1 wt % (added in polymerization) | added | 15.2 | 895 |
| Example 5 | water-absorbing agent (5) | PEG6,000 | 0.1 wt % (added in polymerization) | added | 15.4 | 910 |
| Example 6 | water-absorbing agent (6) | PEG6,000 | 4 wt % (added in polymerization) | added | 13.1 | 1205 |
| Example 7 | water-absorbing agent (7) | PEG1,000 | 0.5 wt % (added in polymerization) | added | 16.5 | 783 |
| Example 8 | water-absorbing agent (8) | PEG2,000 | 0.5 wt % (added in polymerization) | added | 15.3 | 898 |
| Example 9 | water-absorbing agent (9) | PEG monostearate | 0.5 wt % (added in polymerization) | added | 15.9 | 721 |
| Example 10 | water-absorbing agent (10) | PEG6,000 | 0.5 wt % (added in surface treatment) | added | 15.6 | 824 |
| Example 11 | water-absorbing agent (11) | PEG6,000 | 0.5 wt % (added in surface treatment) | added (in surface treatment agent) | 14.8 | 945 |
| Example 12 | water-absorbing agent (12) | PEG600 | 1 wt % (added in polymerization) | added | 15.5 | 650 |
| Comparative example 1 | comparative water-absorbing agent (1) | without PEG | | not added | 16.1 | 331 |
| Comparative example 2 | comparative water-absorbing agent (2) | without PEG | | added | 15.6 | 598 |
| Comparative example 3 | comparative water-absorbing agent (3) | without PEG | | not added | 16.3 | 344 |
| Comparative example 4 | comparative water-absorbing agent (4) | without PEG | | added | 15.9 | 619 |
| Comparative example 5 | comparative water-absorbing agent (5) | PEG6,000 | 1 wt % (added in polymerization) | not added | 18.8 | 226 |
| Comparative example 6 | comparative water-absorbing agent (6) | PEG6,000 | 0.5 wt % (added in surface treatment) | not added | 5.8 | 399 |
| Comparative example 7 | comparative water-absorbing agent (7) | without PEG | | not added | 21.6 | 201 |
| Comparative example 8 | comparative water-absorbing agent (8) | without PEG | | added | 21.4 | 305 |
| Comparative example 9 | comparative water-absorbing agent (9) | PEG6,000 | 1 wt % (added in polymerization) | not added | 21.5 | 195 |
| Comparative example 10 | comparative water-absorbing agent (10) | PEG6,000 | 1 wt % (added in polymerization) | added | 21.3 | 302 |
| Comparative example 11 | comparative water-absorbing agent (11) | without PEG | | not added | 27.7 | 62 |
| Comparative example 12 | comparative water-absorbing agent (12) | without PEG | | added | 26.4 | 111 |
| Comparative example 13 | comparative water-absorbing agent (13) | PEG6,000 | 0.5 wt % (added in polymerization) | not added | 27.0 | 66 |
| Comparative example 14 | comparative water-absorbing agent (14) | PEG6,000 | 0.5 wt % (added in surface treatment) | not added | 26.7 | 69 |

Figure 4:
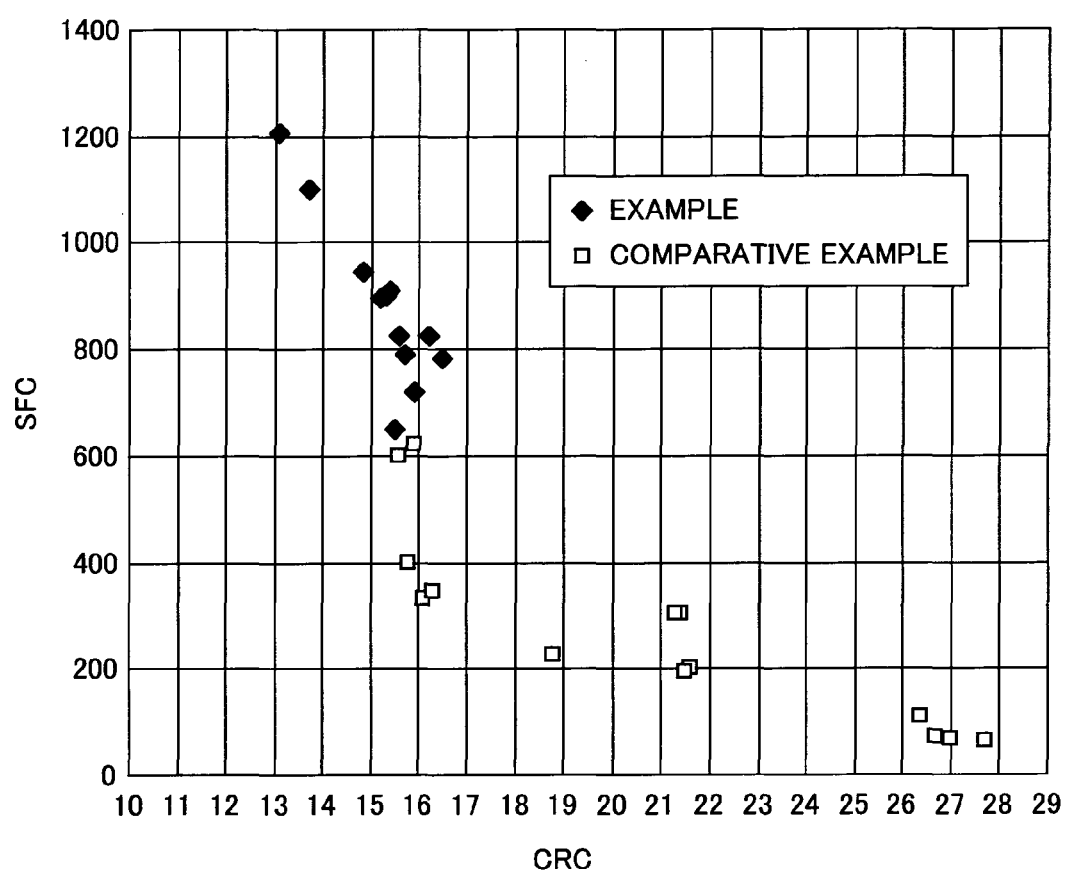
FIG. 4 is a graph indicative of a relation between SFC and CRC obtained in Examples and Comparative examples.

Table 1 and FIG. 4 indicate that the water-absorbing agents (1) to (12) in Examples 1 to 12 that were obtained by adding (i) a compound that includes a constitutional unit derived from polyalkyleneglycol and that is other than an unsaturated monomer and (ii) polyvalent metal salt to water-absorbent resin particles with Centrifuge Retention Capacity (CRC) being 20 g/g or less have higher Saline Flow Conductivity (SFC) than the comparative water-absorbing agents (1) to (6).

Furthermore, the comparative water-absorbing agents (1) to (6) have lower SFC than the water-absorbing agents (1) to (12), which indicates that (i) a compound that includes a constitutional unit derived from polyalkyleneglycol and that is other than an unsaturated monomer and (ii) a polyvalent metal salt are essential.

Furthermore, the comparative water-absorbing agents (7) to (14) indicate that in a case where CRC is 20 g/g or more, even when (i) a compound that includes a constitutional unit derived from polyalkyleneglycol and that is other than an unsaturated monomer and (ii) polyvalent metal salt are added, SFC is less than 400.

INDUSTRIAL APPLICABILITY

According to the present invention, by causing an absorbent core in a sanitary material such as a diaper to include an aqueous liquid-absorbing agent of the present invention, it is possible to diffuse the aqueous liquid in a wider range and to retain an aqueous liquid with an amount larger than that of the aqueous liquid absorbed by the aqueous liquid-absorbing agent. This allows the present invention to be applicable to purposes of sanitary materials and other purposes, such as further thinning the sanitary material, which is very useful.

The invention claimed is:

1. A water-absorbing agent, comprising water-absorbent resin particles obtained by polymerizing an acid group-containing unsaturated monomer,
the water-absorbing agent having Centrifuge Retention Capacity (CRC) ranging from 5 to 20 g/g, and including (i) a compound that includes a constitutional unit derived from polyalkyleneglycol and that is other than an unsaturated monomer, said compound having a weight-average molecular weight ranging from 1000 to 6000 and (ii) polyvalent metal salt, and
the compound including no radical polymerizable group, and being free without forming a chemical bond with the water-absorbent resin particles or being separable from the water-absorbent resin particles and without forming an internal crosslinked structure in the water-absorbent resin particles,
the compound included in the water-absorbing agent falling within a range of 0.05 to 5 mass % with respect to the water-absorbing agent.

2. The water-absorbing agent as set forth in claim 1, wherein the water-absorbent resin particles are surface-crosslinked.

3. The water-absorbing agent as set forth in claim 1, wherein Saline Flow Conductivity (SFC) is 400 cm$^3$·s·10$^{-7}$/g or more.

4. The water-absorbing agent as set forth in claim 1, wherein the water-absorbent resin particles are obtained by polymerization in a presence of an internal crosslinking agent containing an unsaturated monomer including a constitutional unit derived from polyalkyleneglycol.

5. The water-absorbing agent as set forth in claim 1, wherein:
the compound including no radical polymerizable group, and being free without forming a chemical bond with the water-absorbent resin particles or being separable from the water-absorbent resin particles and without forming an internal crosslinked structure in the water-absorbent resin particles means that:
the compound includes no radical polymerizable group, and at least 50% of the compound exist without forming a covalent bond with the water-absorbent resin particles.

* * * * *